US006759243B2

(12) United States Patent
Kranz et al.

(10) Patent No.: US 6,759,243 B2
(45) Date of Patent: Jul. 6, 2004

(54) HIGH AFFINITY TCR PROTEINS AND METHODS

(75) Inventors: David M. Kranz, Champaign, IL (US); K. Dane Wittrup, Chestnut Hill, MA (US); Phillip D. Holler, Champaign, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 105 days.

(21) Appl. No.: 09/731,242

(22) Filed: Dec. 6, 2000

(65) Prior Publication Data

US 2002/0058253 A1 May 16, 2002

Related U.S. Application Data

(63) Continuation-in-part of application No. 09/009,388, filed on Jan. 20, 1998
(60) Provisional application No. 60/169,179, filed on Dec. 6, 1999.

(51) Int. Cl.⁷ ............................. C12N 5/10; C12N 5/08; C07K 14/725
(52) U.S. Cl. ............................. 435/372.3; 435/320.1; 435/325; 435/366; 435/372; 530/350
(58) Field of Search ..................... 435/320.1, 325, 435/366, 372, 372.3; 530/350

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,927,193 A | 12/1975 | Hansen et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,331,647 A | 5/1982 | Goldenberg |
| 4,348,376 A | 9/1982 | Goldenberg |
| 4,361,544 A | 11/1982 | Goldenberg |
| 4,366,241 A | 12/1982 | Tom et al. |
| 4,444,744 A | 4/1984 | Goldenberg |
| 4,468,457 A | 8/1984 | Goldenberg et al. |
| 4,640,561 A | 2/1987 | George |
| 4,713,332 A | 12/1987 | Mak |
| 4,831,122 A | 5/1989 | Buchsbaum et al. |
| 4,873,190 A | 10/1989 | Saito et al. |
| 4,874,845 A | 10/1989 | Saito et al. |
| 4,885,248 A | 12/1989 | Ahlquist |
| 4,923,799 A | 5/1990 | Mak |
| 4,946,778 A | 8/1990 | Ladner et al. |
| 4,970,296 A | 11/1990 | Saito et al. |
| 5,013,650 A | 5/1991 | Carty |
| 5,024,940 A | 6/1991 | Brenner et al. |
| 5,059,413 A | 10/1991 | Reardan et al. |
| 5,101,827 A | 4/1992 | Goldenberg |
| 5,173,410 A | 12/1992 | Ahlquist |
| 5,185,250 A | 2/1993 | Brenner et al. |
| 5,223,409 A | 6/1993 | Ladner et al. |
| 5,225,539 A | 7/1993 | Winter |
| 5,258,289 A | 11/1993 | Davis |
| 5,258,498 A | 11/1993 | Huston et al. |
| 5,260,203 A | 11/1993 | Ladner et al. |
| 5,299,253 A | 3/1994 | Wessels |
| 5,316,922 A | 5/1994 | Brown |
| 5,316,925 A | 5/1994 | Davis et al. |
| 5,340,921 A | 8/1994 | Brenner et al. |
| 5,348,867 A | 9/1994 | Georgiou et al. |
| 5,403,484 A | 4/1995 | Ladner et al. |
| 5,411,873 A | 5/1995 | Adams |
| 5,427,908 A | 6/1995 | Dower |
| 5,466,788 A | 11/1995 | Ahlquist |
| 5,482,858 A | 1/1996 | Huston et al. |
| 5,498,530 A | 3/1996 | Schatz |
| 5,500,360 A | 3/1996 | Ahlquist et al. |
| 5,510,240 A | 4/1996 | Lam |
| 5,571,698 A | 11/1996 | Ladner |
| 5,580,717 A | 12/1996 | Dower et al. |
| 5,580,961 A | 12/1996 | Saito et al. |
| 5,601,822 A | 2/1997 | Brenner et al. |
| 5,602,242 A | 2/1997 | Ahlquist et al. |
| 5,614,192 A | 3/1997 | Vandenbark |
| 5,624,817 A | 4/1997 | Miller et al. |
| RE35,500 E | 5/1997 | Rhodes |
| 5,627,060 A | 5/1997 | Ahlquist et al. |
| 5,633,447 A | 5/1997 | Ahlquist et al. |
| 5,635,363 A | 6/1997 | Altman et al. |
| 5,670,353 A | 9/1997 | Ahlquist et al. |
| 5,723,286 A | 3/1998 | Dower et al. |
| 5,723,309 A | 3/1998 | Bonneville |
| 5,723,323 A | 3/1998 | Kauffman et al. |
| 5,733,743 A | 3/1998 | Johnson et al. |

(List continued on next page.)

FOREIGN PATENT DOCUMENTS

| | | |
|---|---|---|
| AU | B7 195 191 | 3/1992 |
| EP | 067553 | 12/1982 |

(List continued on next page.)

OTHER PUBLICATIONS

Ahlquist et al., "Viral Vectors," *Cold Spring Harbor Laboratory*, New York 183–189 (1988).

(List continued on next page.)

*Primary Examiner*—David Guzo
(74) *Attorney, Agent, or Firm*—Greenlee, Winner and Sullivan, P.C.

(57) ABSTRACT

T cell receptors (TCRs) that have higher affinity for a ligand than wild type TCRs are provided. These high affinity TCRs are formed by mutagenizing a T cell receptor protein coding sequence to generate a variegated population of mutants of the T cell receptor protein coding sequence; transforming the T cell receptor mutant coding sequence into yeast cells; inducing expression of the T cell receptor mutant coding sequence on the surface of yeast cells; and selecting those cells expressing T cell receptor mutants that have higher affinity for the peptide/MHC ligand than the wild type T cell receptor protein. The high affinity TCRs can be used in place of an antibody or single chain antibody.

23 Claims, 15 Drawing Sheets

U.S. PATENT DOCUMENTS

| | | |
|---|---|---|
| 5,738,996 A | 4/1998 | Hodges |
| 5,763,192 A | 6/1998 | Kauffman et al. |
| 5,763,733 A | 6/1998 | Whitlow et al. |
| 5,767,260 A | 6/1998 | Whitlow et al. |
| 5,780,225 A | 7/1998 | Wigler et al. |
| 5,789,208 A | 8/1998 | Sharon |
| 5,814,476 A | 9/1998 | Kauffman et al. |
| 5,817,483 A | 10/1998 | Kauffman et al. |
| 5,824,483 A | 10/1998 | Houston, Jr. et al. |
| 5,824,514 A | 10/1998 | Kauffman et al. |
| 5,837,477 A | 11/1998 | Germain et al. |
| 5,837,500 A | 11/1998 | Ladner et al. |
| 5,840,304 A | 11/1998 | Davis et al. |
| 5,858,657 A | 1/1999 | Winter et al. |
| 5,861,156 A | 1/1999 | George et al. |
| 5,866,344 A | 2/1999 | Georgiou |
| 5,866,363 A | 2/1999 | Pieczenik |
| 5,869,620 A | 2/1999 | Whitlow et al. |
| 5,871,907 A | 2/1999 | Winter et al. |
| 5,871,974 A | 2/1999 | Huse |
| 5,882,945 A | 3/1999 | Saito et al. |
| 5,900,476 A | 5/1999 | Ruggeri et al. |
| 5,948,409 A | 9/1999 | Germain et al. |
| 5,969,108 A | 10/1999 | McCafferty et al. |
| 5,977,321 A | 11/1999 | Saito et al. |
| 6,017,732 A | 1/2000 | Jespers et al. |
| 6,027,910 A | 2/2000 | Klis et al. |
| 6,087,096 A * | 7/2000 | Dau et al. .................. 435/6 |
| 6,114,147 A | 9/2000 | Frenken et al. |
| 6,232,099 B1 | 5/2001 | Chapman et al. |
| 6,319,713 B1 * | 11/2001 | Patten et al. ............ 435/440 |
| 6,416,971 B1 * | 7/2002 | Reinherz et al. .......... 435/69.1 |

FOREIGN PATENT DOCUMENTS

| | | |
|---|---|---|
| EP | 174759 | 3/1986 |
| EP | 194809 | 9/1986 |
| EP | 278667 | 8/1988 |
| EP | AO 425 004 | 5/1991 |
| EP | AO 479 180 | 4/1992 |
| EP | 0 672 754 A1 | 3/1993 |
| EP | AO 573 767 | 12/1993 |
| EP | 0 436 597 B1 | 4/1997 |
| JP | 61/158443 | 7/1986 |
| JP | 63-14693 | 1/1988 |
| JP | 63/200789 | 8/1988 |
| WO | WOA89 08145 | 9/1989 |
| WO | WOA90 12107 | 10/1990 |
| WO | WO 91/15587 | 4/1991 |
| WO | WOA91 13994 | 9/1991 |
| WO | WO 92/18618 | 10/1992 |
| WO | WO 93/03161 | 2/1993 |
| WO | WO94/01567 | 1/1994 |
| WO | WO94/18330 | 8/1994 |
| WO | WO 95/21248 | 2/1995 |
| WO | WO 9602649 A1 | 2/1996 |
| WO | WO 96/12027 | 4/1996 |
| WO | 98 39482 A | 9/1998 |
| WO | WO98/49286 | 11/1998 |
| WO | 99 36569 A | 7/1999 |

OTHER PUBLICATIONS

Ahlquist and Pacha, *Physiol. Plant.* 79:163–167 (1990).

Barton et al., *Plant Physiol.* 85:1103–1109 (1987).

Bruening, G., "Comovirus group, C.M.I./A.A.B. Descriptions of plant viruses," No. 199. *Wm. Culross and Son Ltd., Coupar Angus, Perthshire, Scotland.* (1978).

Butler and Mayo, "Molecular architecture and assembly of tobacco mosaic virus particles," *The molecular biology of the positive strand RNA Viruses, Academic Press, London*:237–257 (1987).

Cassidy and Nelson, *Phytopathology* 80:1037 (1990).

Chapman et al., *Plant Journal* 2:549 (1992).

Charoenvit et al., "Inability of malaria vaccine to induce antibodies to a protective epitope within its sequence," *Science* 251:668–671 (1991).

Charoenvit et al., "Monoclonal, but not polyclonal, antibodies protect against *Plasmodium yoeli* sporozoites," *J. Immunol.* 146:1020–1025 (1991).

Citovsky and Zambryski, *BioEssays* 13:373–379 (1991).

Culver et al., in press, *Virology*.

Dawson and Hilf, *Ann. Rev. Plant Physiol. Plant Mol. Biol.* 43:527–555 (1992).

Dawson et al., "cDNA cloning of the complete genome of tobacco mosaic virus and production of infectious transcripts," *Proc. Natl. Acad. Sci. USA* 83:1832–1836 (1986).

Dawson et al., "Modifications of the tobacco mosaic virus coat protein gene affecting replication, movement, and symptomatology," *Phytopathol.* 78:783–789 (1988).

Dawson et al., "A tobacco mosaic virus–hybrid expresses and loses an added gene," *Virology* 172:285–292 (1989).

Dawson, *Adv. Virus Res.* 38:307–342 (1990).

Dawson, *Virology* 186:359–367 (1992).

Deom et al., "Plant Virus Movement Proteins," *Cell* 69:221–224 (1992).

Deom et al., *Science* 237:389–394 (1987).

Dolja et al., *Proc. Natl. Acad. Sci. USA* 89:10208 (1992).

Donson et al., "Systemic expression of a bacterial gene by a tobacco mosaic virus–based vector," *Proc. Natl. Acad. Sci. USA* 88:7204–7208 (1991).

Dunsmuir et al., "Stability of introduced genes and stability of expression," Plant Molecular Biology Manual, *Kluwer Academic Publishers, Dordrecht, The Netherlands*:C1:1–17 (1988).

Fitchen et al., "Plant virus expressing hybrid coat protein with added murine epitope elicits autoantibody response," *Vaccine* 13:1051–1057 (1995).

French et al., "Bacterial ene inserted in an engineered RNA virus: Efficient expression in monocotyledonous plant cells," *Science* 231:1294–1297 (1986).

Gibbs, A.J., "Tobamovirus group, C.M.I./A.A.B. Descriptions of plant viruses," No. 184. *Wm. Culross and Son Ltd., Coupar Angus, Perthshire, Scotland* (1977).

Goelet et al., "Nucleotide sequence of tobacco mosaic virus RNA," *Proc. Natl. Acad. Sci. USA* 79:5818–5822 (1982).

Gooding, Jr., G.V., and Hebert, T.T., "A simple technique for purification of tobacco mosaic virus in large quantities," *Phytopathology* 57:1285 (1967).

Hamamoto et al., "A new tobacco mosaic virus vector and its use for the systemic production of angiotensin–I–converting enzyme inhibitor in transgenic tobacco and tomato," *Bio/Technology* 11:930–932 (1993).

Haynes et al., "Development of a genetically–engineered, candidate polio vaccine employing the self–assembling properties of the tobacco mosaic virus coat protein," *Bio/Technology* 4:637–641 (1986).

Horsch et al., "Leaf disc transformation," Plant Molecular Biology Manual, *Kluwer Academic Publishers, Dordrecht, The Netherlands*:A5:1–9 (1988).

Jagadish et al., "High Level Production of Hybrid otybirus-like Particles Carrying Repetitive Copies of Foreign Antigens in *Escherichia coli*," *Bio/Technology* 11:1166–1170 (1993).

Joshi and Joshi, *FEBS Letters* 281:1–8 (1991).

Joshi et al., "BSMV genome mediated expression of a foreign gene in dicot and monoclonal plant cells," *EMBO J.* 9:2663–2669 (1990).

Jupin et al., *Virology* 178:273–280 (1990).

Kearny et al., *Virology* 192:000–000 (in press) (1993).

Krebbers et al., "Prospects and progress in the production of foreign proteins and peptides in plants," *Plant Protein Engineering.* (P.R. Shewry and S. Gutteridge, eds.), Cambridge University Press, Cambridge, pp. 315–325 (1992).

Kumagai et al., "Rapid, high level expression of biologically active $_\alpha$–trichosanthin in transfected plants by a novel RNA viral vector," *Proc. Natl. Acad. Sci USA* 90:427–430 (1993).

Larkins et al., *J. Cell. Biochem. Suppl. 0*(*9 Part C*):264 (1985).
Martelli, *Plant Disease 76*:436 (1992).
Mason et al., "Expression of hepatitis B surface antigen in transgenic plants," *Proc. Natl. Acad. Sci. USA 89*:11745–11749 (1992).
Ogawa et al., *Virology 185*:580–584 (1991).
Ow et al., *Science 234*:856 (1986).
Pelham, H.R.B., "Leaky UAG termination codon in tobacco mosaic virus RNA," *Nature 272*:469–471 (1978).
Porta et al., "Development of Cowpea Mosaic Virus as a High–Yielding System for the Presentation of Foreign Peptides," *Virology 202*:949–955 (1994).
Potrykus, *Ann. Rev. Plant Physiol. Plant Mol. Biol. 42*:205–225 (1991).
Raffo and Dawson, "Construction of Tobacco Mosaic Virus Subgenomic Replicons that are Replicated and Spread Systemically in Tobacco Plants," *Virology 184*:277–289 (1991).
Rowlands et al., eds., *American Press, London*, pp. 237–257 (1987).
Saito et al., *Virology 176*:329–336 (1990).
Shaw, "Chloramphenicol acetyltransferase from chloramphenicol–resistant bacteria," *Methods in Enzymology 53*:737–755 (1975).
Skuzeski et al., "The signal for a leaky UAG stop codon in several plant viruses includes the two downstream codons," *J. Mol. Biol. 218*:365–373 (1991).
Takamatsu et al., *J. Virol. 65*:1619–1622 (1991).
Takamatsu et al., *J. Virol. 64*:3686–3693 (1990).
Takamatsu et al., "Expression of bacterial chloramphenicol acetyltransferase gene in tobacco plants mediated by TMV–RNA," *EMBO J. 6*:307–311 (1987).
Takamatsu et al., "Production of enkephalin in tobacco protoplasts using tobacco mosaic virus RNA vector," *FEBS Lett. 269*:73–76 (1990).
Turpen and Dawson, "Transgenic Plants, Fundamentals and Applications," *Marcel Dekkar, New York*, pp. 195–217 (1992).
Turpen, "Ph.D. Dissertation," *University of California, Riverside*, pp. 72–87 (1992).
Turpen, "Ph.D. Dissertation," *University of California, Riverside*, pp. 85–105 (1992).
Turpen, "Ph.D. Dissertation," *University of California, Riverside*, pp. 106–132 (1992).
Turpen and Dawson, "Amplification, movement and expression of genes in plants by viral–based vectors," *Marcel Dekkar, New York*, pp. 195–217.
Turpen, T.H., "a Molecular Genetic Analysis of Host/Viral Interactions, Implications for the Use of Plant RNA Viruses as Gene Vectors," *Chem. Abstracts 120*(*9*):97427 (1992).
Turpen et al., "Malarial Epitopes Expressed on the Surface of Recombinant Tobacco Mosaic Virus," *Bio/Technology 10*:53–57 (1995).
Usha et al., "Expression of an animal virus antigenic site on the surface of a plantvirus particle," *Virology 197*:366–374 (1993).
Van Haute et al., *EMBO J. 2*:411–417 (1983).
Von Kammen et al., "Cowpea mosaic virus, C.M.I./A.A.B. Descriptions of plant viruses," No. 197, *Wm. Culross and Son Ltd., Coupar Angus, Perthshire, Scotland*, pp. 1–5 (1978).
Venton and Schell, *NAR 13*:6981 (1985).
Walden and Schell, *Eur. J. Biochem. 192*:563–576 (1990).
Weiss et al., "A T cell clone directed at the circumsporozoite protein which protects mice against both *Plasmodium yoelli* and *Plasmodium berghei," J. Immunol. 149*:2103–2109 (1992).
Yamaya et al., *Mol. Gen. Genet. 211*:520–525 (1988).
Zaitlin et al., "Tobacco mosaic virus (type strain), C.M.I./A.A.B. Descriptions of plant viruses," No. 151, *Wm. Culross and Son Ltd., Coupar Angus, Perthshire, Scotland*, pp. 1–6 (1975).
Zaitlin and Hull, *Ann. Rev. Physiol. 38*:291–315 (1987).
Zambryski et al., *EMBO J. 2*:2143–2150 (1983).
Weidanz, Jon A. et al. (Aug. 1998), "Display of functional αβ single–chain T–cell receptor molecules on the surface of bacteriophage" *Journal of Immunological Methods* 221:59–76.
Shusta, E.V. et al. (1999) "Yeast Polypeptide Fusion Surface Display Levels Predict Thermal Stability and Soluble Secretion Efficiency" *Academic Press* 292:949–956.
Lake, D.F. et al. (Jan. 1999) "Construction and binding analysis of recombinant single–chain TCR derived from tumor–infiltrating lymphocytes and a cytotoxic T lymphocyte clone directed against MAGE–1" *International Immunology* 11:745–751.
Kumar, V. et al. (1997) "Recombinant T Cell Receptor Molecules Can Prevent and Reverse Experimental Autoimmune Encephalomyelitis" *The Journal of Immunology* 159:5150–5156.
Alam et al., (Jun. 1996), *"T–cell–receptor Affinity and Thymocyte Positive Selection," Nature 381:616–620.*
Anand, R. et al. (1992), "Progress in developing methylotrophic yeasts as expression systems." *TIBTECH* 10:413–417.
Bentley, G.A. and Mariuzza, R.A., (1996), *"The Structure of the T Cell Antigen Receptor," Annu. Rev. Immunol. 14:563–590.*
Boder, E.T. and Wittrup, K.D., (1997), *"Yeast surface display for screening combinatorial ploypeptide libraries." Nature Biotech,. 15*(*6*)*:553–557.*
Boder, E.T. and Wittrup, K.D. (1995), *"A Yeast Surface Display System for in vitro Affinity Maturation of Antibodies," Protein Interactions*, Jun. 1–4, 1995, Beckman Institute, University of Illinois, Urbana (Abstract Only).
Buckholz, R.G. and Gleeson, M.A.G. (1991), "Yeast Systems for the Commercial Production of Heterologous Proteins," *Bio/Technol*. 9:1067–1072.
Bjorkman, P.J., (Apr. 1997), "MHC Restriction in Three Dimensions: A View of T Cell Receptor/Ligand Interactions," *Cell* 89:167–170.

Clackson et al., (Apr. 1991), "Making Antibody Fragments Using Phage Display Libraries," *Nature* 352:624–628.

Cregg, J.M. et al. (1993), "Recent Advances in the Expression of Foreign Genes in *Pichia pastoris*," *Bio/Technol.* 11:905–910.

Faber, K.N. et al. (1995), "*Review: Methylotrophic Yeasts as Factories for the Production of Foreign Proteins,*" *Yeast* 11:1331–1344.

Fremont et al., (1996), "Biophysical Studies of T–cell Receptors and Their Ligands," *Curr. Opin. Immunol.* 8:93–100.

Hawkins, R.E. et al. (1992), "*Selections of Phage Antibodies by Binding Affinity Mimicking Affinity Maturation,*" *J. Mol. Biol.* 226:889–896.

Hawkins, R.E. et al. (1993), "*The Contribution of Contact and Non–contact Residues of Antibody in the Affinity of Binding to Antigen,*" *J. Mol. Biol.* 234:958–964.

Jung, S. and Plückthun (1997), "*Improving in vivo folding and stability of a single–chain Fv antibody fragment by loop grafting,*" *Protein Eng.* 10(8):959–966.

Kieke, M.C. et al. (1997), "*Isolation of anti–T cell receptor scFv mutants by yeast surface display,*"*Protein Eng.* 10(11):1303–1310.

Klis, F.M. (1994). "*Review: Cell Wall Assembly in Yeast,*" *Yeast* 10:851–869.

Knappik, A. and Plückthun, A. (1995), "*Engineered turns of a recombinant antibody improve its in vivo folding,*" *Protein Eng.* 8(1):81–89.

Lipke, P.N. and Kurjan, J., (Mar. 1992), "Sexual Agglutination in Budding Yeasts: Structure, Function, and Regulation of Adhesion Glycoproteins," *Microbiological Reviews* pp. 180–194.

Lyons et al., (Jul. 1996), "A TCR Binds to Antagonist Ligands with Lower Affinities and Faster Dissociation Rates Than to Agonists," *Immunity* 5:53–61.

Margulies, D.H., (Jun. 1996), "*An Affinity for Learning,*" *Nature* 381:558–559.

Marx, J. (Jan. 1995), "The T Cell Receptor Begins to Reveal Its Many Facets," *Science* 267:459–460.

Matsui et al., (Dec. 1991), "Low Affinity Interaction of Peptide–MHC Complexes with T Cell Receptors," *Science* 254:1788–1791.

Matsui et al., (*Dec.* 1994), "*Kinetics of T–cell Receptor Binding to Peptide/I–E$^k$ Complexes : Correlation of the Dissociation Rate with T–cell Responsiveness*," *Proc. Natl. Acad. Sci. USA* 91:12862–12866.

Nieba, L. et al. (1997). "Disrupting the hydrophobic patches at the antibody variable/constant domain interface: improved in vivo folding and physical characterization of an engineered scFv fragment," Protein Eng. 10(4):435–444.

O'Herrin et al., (Oct. 1997), "Analysis of the Expression of Peptide–Major Histocompatibility Complexes Using High Affinity Soluble Divalent T Cell Receptors," *J. Exp. Med* 186:1333–1345.

Reich et al., (Jun. 1997), "Ligand–specific Oligomerization of T–cell Receptor Molecules," *Nature* 387:617–620.

Ridder, R. et al. (1995), "Generation of Rabbit Monoclonal Antibody Fragments from a Combinatorial Phage Display Library and Their Production in the Yeast *Pichia pastoris*," *Bio/Technol.* 13:255–259.

Romanos, M. (1995), "Advances in the use of *Pichia pastoris* for high–level gene expression," *Curr. Opinion in Biotechnol.* 6:527–533.

Romanos et al., (1992), "Foreign Gene Expression in Yeast: a Review," *Yeast* 8:423–488.

Schlueter et al., (1996), "*Specificity and Binding Properties of a Single–chain T Cell Receptor,*" *J. Mol. Biol.* 256:859–869.

Schreuder et al., (Apr. 1996), "*Immobilizing Proteins on the Surface of Yeast Cells,*" *TIBTECH* 14:115–120.

Schodin et al., (1996), "*Binding Properties and Solubility of Single–Chain T Cell Receptors Expressed in E. coli,*" *Molec. Immunol.* 33(9):819–829.

Sudbery, P.E. (1994), "*The Non–Saccharomyces Yeasts,*" *Yeast* 10:1707–1726.

Syrulev et al., (*Dec.* 1995), "*The Law of Mass Action Governs Antigen–stimulated Cytolytic Activity of $CD8^{+cytotoxic}$ $T$ $Lymphocytes$,*" *Proc. Natl. Acad. Sci. USA* 92:11990–11992.

Ulrich et al. (Dec. 1995), "*Expression Studies of Catalytic Antibodies,*" Proceed. Natl. Acad. Sci. 92:11907–11911.

van der Vaart (Sep. 1965), "*Identification and Characterization of Cell Wall Proteins of Saccharomyces ceevisiae,*" Thesis. ISBN 90–393–1498–5 pp. 1–138.

Weber et al., (Apr. 1992), "*Specific Low–affinity Recognition of Major Histocompatibility Complex Plus Peptide by Soluble T–cell Receptor,*" *Nature* 356:793–796.

Alam, S.M. et al., (Feb. 1999), "Qualitative and Quantitative Differences in T Cell Receptor Binding of Agonist and Antagonist Ligands," Immunity 10:227–237.

Alberti, S., (1996), "A high affinity T cell receptor?," Immunol. Cell Biol. 74:292–297.

Altschul, S.F. et al., " Gapped BLAST and PSI–BLAST: a new generation of protein database search programs" (Sep. 1997) Nucleic Acids Research 25(17):2278–3402.

Baldwin, R.W. and Byers, V.S., (Editors) (1985), *Monoclonal Antibodies for Cancer Detection and Therapy*,London Academic Press pp. 159–179.

Beeson, C. et al., (Aug. 1996), "Early Biochemical Signals Arise from Low Affinity TCR–Ligand Reactions at the Cell–Cell Interface," J. Exp. Med. 184:777–782.

Bevan, M.J., "In Thymic Selection, Peptide Diversity Gives and Takes Away" (Aug. 1997), Immunity 7:175–178.

Boder, E.T. et al., " Directed Evolution of Antibody Fragments with Monovalent Femtomolar Antigen–binding Affinity" (Sep. 2000) Proc. Nat'l. Acad. Sci. USA 97(20):10701–10705.

Boder, E.T. and Wittrup, K.D., (Feb. 1998), "Optimal Screening of Surface–Displayed Polypeptide Libraries," Biotech. Progress 14(1):55–62.

Boniface, J.J. et al., (Sep. 1999), "Thermodynamics of T cell receptor binding to peptide–MHC: Evidence for a general mechanism of molecular scanning" Proc. Natl. Acad. Sci. *USA* 96:11446–11451.

Buchwalder, A. et al., (1994), "Immunochemical and Molecular Analysis of Antigen Binding to Lipid Anchored and Soluble Forms of an MHC Independent Human α/β T Cell Receptor," Mol. Immunol. 31(11):857–872.

Callan, M.F. et al., (1995), "Selection of T cell receptor variable gene–encoded amino acids on the third binding site loop: a factor influencing variable chain selection in a T cell response," Eur. J. Immunol. 25:1529–1534.

Cheng, Y.C., "Relationship Between The Inhibition Constant ($K_1$) and the Concentration of Inhibitor Which Causes 50 Per Cent Inhibition ($I_{50}$) of an Enzymatic Reaction" (1973), Biochem. Pharm. 22:3099–3108.

Cho, B.K. et al., "A yeast surface display system for the discovery of ligands that trigger cell activation." (Nov. 1988) J. Immunol Methods (Netherlands) 220:179–88.

Chung. S. et al., (Dec. 1994), "Functional three–domain single–chain T–cell receptors," Proc. Natl. Acad. Sci. USA 91:12654–12658.

Clackson, T. et al., (Aug. 1991) "Making antibody fragments using phage display libraries" Nature 352:624–628.

Dal Porto, J. et al., (1993), "A soluble divalent class I major histocompatibility complex molecule inhibits alloreactive T cells at nanomolar concentrations" Proc. Natl. Acad. Sci. USA 90:6671–6675.

Davis, M.M. and Bjorkman, D.J., (Aug. 1988), "T–cell antigen receptor genes and T–cell recognition," Nature 334:395–402.

Davis et al., (Annual–1998), "Ligand Recognition by $\alpha\beta$ T Cell Receptors," Annu. Rev. Immunol. 16:523–544.

Davis, M.M. and Chien, Y., (1993), "Topology and affinity of T–cell receptor mediated recognition of peptide–MHC complexes," Curr. Opin. Immunol. 5:45–49.

de Kruif, J. and Logtenberg, T., (Mar. 1996), "Leucine Zipper Dimerized Bivalent and Bispecific scFv Antibodies from a Semi–synthetic Antibody Phage Display Library," Amer. Soc. Biochem. Mol. Biol. 271(13):7630–7634.

Eisen, H. N. et al., (1996)," Antigen–Specific T–Cell Receptors And Their Reactions With Complexes Formed By Peptides With Major Histocompatibility Complex Proteins" Adv. Protein Chem. 49:1–56.

Faber, K.N. et al., (1995), "Review: Methylotrophic Yeasts as Factories for the Production of Foreign Proteins" Yeast 11:1331–1344.

Foote, J. and Eisen, H.N., (Sep. 2000) "Breaking the affinity ceiling for antibodies and T cell receptors" PNAS 97(20):10679–10681.

Furukawa, k. et al., "Junctional Amino Acids Determine the Maturation Pathway of an Antibody" (Sep. 1999), Immunity 11:329–338.

Ganju, R.K. et al., (Dec. 1992), "Similarity between fluorescein–specific T–cell receptor and antibody in chemical details of antigen recognition," Proc. Natl. Acad. Sci. USA 89:11552–11556.

Garcia, K.C. et al. "An $\alpha$B T Cell Receptor Structure at 2.5 Åand Its Orientation in the TCR–MHC Complex" (Oct. 1996), Science 274:209–219.

Garcia, K.C. et al., "CD8 enhances formation of stable T–cell receptor/MHC class I molecule complexes" (Dec. 1996), Nature 384:577–584.

Garcia, K.C. et al., (Dec. 1997), "$\alpha\beta$ T cell receptor interactions with syngeneic and allogeneic ligands: Affinity measurements and crystallization," Proc. Natl. Acad. Sci. USA 94:13838–13843.

Garcia, K.C. et al., "Structural Basis of Plasticity in T Cell Receptor Recognition of a Self Peptide–MHC Antigen" (Feb. 1998) Science 279:1166–1172.

Gascoigne, N.R. et al., (May 1987), "Secretion of a chimeric T–cell receptor–immunoglobulin protein," Proc. Natl. Acad. Sci. USA 84:2936–2940.

Gellissen, G. et al., (1992) "Progress in developing methylotrophic yeasts as expression systems" Tibtech 10:413–417.

Geitz, R.D. et al., (1995), "Studies on the Transformation of Intact Yeast Cells by the LiAc/SS–DNA/PEG Procedure" Yeast 11:355–360.

Hare, B.J. et al., (Jun. 1999), "Structure, specificity and CDR mobility of a class II restricted single–chain T–cell receptor" Nat. Struct. Biol. 6:574–581.

Hilyard, K.L. et al., (Sep. 1994), "Binding of soluble natural ligands to a soluble human T–cell receptor fragment produced in *Escherichia coli*," Pro. Natl. Acad. Sci. USA 91:9057–9061.

Holler, P.D. et al., (May 2000), "In vitro evolution of a T cell receptor with high affinity for peptide/MHC,"PNAS 97(10):5387–5392.

Huse, W. D. et al., (Dec. 1989), "Generation of a Large Combinatorial Library of the Immunoglobulin Repertoire in Phage Lambda," Science 246:1275–1281.

Jorgensen, J.L. et al., (Jan. 1992), "Mapping T–cell receptor–peptide contacts by variant peptide immunization of single–chain transgenics," Nature 355:224–230.

Kappler, J. et al., (Aug. 1994), "Binding of a soluble $\alpha\beta$ T–cell receptor to superantigen/major histocompatibility complex ligands," Proc. Natl. Acad. Sci. USA 91:8462–8466.

Kieke, M.C. et al., (May 1999), "Selection of functional T cell receptor mutants from a yeast surface–display library," Proc. Natl. Acad. Sci. USA 96(10):5651–5656.

Kipriyanov, S. M. et al., (Apr. 1997), "Two amino acid mutations in an anti–human CD3 single chain Fv antibody fragment that affect the yield on bacterial secretion but not the affinity," Protein Eng. 10(4):445–453.

Kowalski, J. M. et al., (Feb. 1998), "Secretion efficiency in *Saccharomyces cerevisiae* of bovine pancreatic trypsin inhibitor mutants lacking disulfide bonds is correlated with thermodynamic stability," Biochemistry 37(5):1264–1273.

Kowalski, J.M. et al., (Jul. 1998), "Protein folding stability can determine the efficiency of escape from endoplasmic reticulum quality control," J. Biol. Chem. 273(31):19453–19458.

Letourneur, F. and Malissen, B., (1989), "Derivation of a T cell hybridoma variant deprived of functional T cell receptor a and b chain transcripts reveals a nonfunctional a–mRNA of BW5147 origin" Eur. J. Immunol. 19(12):2269–2274.

Manning, T. C. et al., (Apr. 1998), "Alanine Scanning Mutagenesis of an $\alpha\beta$ T cell Receptor: Mapping the Energy of Antigen Recognition," Immunity 8:413–425.

Manning et al., (Feb. 1999), "Effects of complementarity determining region mutations on the affinity of alpha/beta T cell receptor: measuring the energy associated with CD4/CD8 repertoire skewing," J. Exp. Med. 189(3):461–470.

Marks, J.D. et al., (Aug. 1992), "Molecular Evolution of Proteins on Filamentous Phage," J. Biol. Chem. 267(23):16007–16010.

Marks, J.D. et al., (1991), "By–passing Immunization. Human Antibodies from V–gene Libraries Displayed on Phage," J. Mol. Biol. 222:581–597.

Martineau, P. et al., (Jul. 1998), "Expression of an antibody fragment at high levels in the bacterial cytoplasm," J. Mol. Biol. 280(1):117–127.

McCafferty, J. et al., (Dec. 1990), "Phage antibodies: filamentous phage displaying antibody variable domains," Nature 348:552–554.

Novotny, J. et al., (Oct. 1991), "A soluble, single–chain T–cell receptor fragment endowed with antigen–combining properties," Proc. Natl. Acad. Sci. USA 88:8646–8650.

Nieba, L. et al., (Apr. 1997), "Disrupting the hydrophobic patches at the antibody variable/constant domain interface: improved in vivo folding and physical characterization of an engineered scFv fragment," Protein Eng. 10(4):435–444.

O'Herrin, S.M. et al., (Oct. 1997), "Analysis of the Expression of Peptide–Major Histocompatibility Complexes Using High Affinity Soluble Divalent T Cell Receptors," J. Exp. Med 186:1333–1345.

Olsnes, S. and Pihl, A., "Chimeric Toxins" (1982), Pharmac. Ther. 25:355–381.

Rabinowitz et al., (Feb. 1996), Kinetic discrimination in T–cell activation Proc. Natl. Acad. Sci. USA 93:1401–1405.

Sant' Angelo, D.B. et al., (Apr. 1996), "The Specificity and Orientation of a TCR to its Peptide–MHC Class II Ligands," Immunity 4:367–376.

Schlueter, C.J. et al., (1996), "A Residue in the Center of Peptide QL9 Affects Binding to Both $L^d$ and the T Cell Receptor$^1$," J. Immunol. 157:4478–4485.

Schneck, J. et al., (Jan. 1989), "Inhibition of an Allospecific T Cell Hybridoma by Soluble Class I Proteins and Peptides: Estimation of the Affinity of a T Cell Receptor for MHC," Cell 56:47–55.

Schodin, B.A. and Kranz, D.M., (Dec. 1993), "Binding Affinity and Inhibitory Properties of a Single–Chain Anti–T Cell Receptor Antibody," J. Biol. Chem. 268(34):25722–25727.

Schodin, B.A. et al., (1996) "Binding Properties and solubility of single–chain T cell receptors expressed in *E. coli*" Immun.33(9):819–829.

Seibel, J.L. et al., (Jun. 1997), "Influence of the $NH_2$–terminal Amino Acid of the T Cell Receptor α Chain on Major Histocompatibility Complex (MHC) Class II + Peptide Recognition," J. Exp. Med. 185(11):1919–1927.

Seth, A. et al., (May 1994), "Binary and ternary complexes between T–cell receptor, class II MHC and superantigen in vitro," Nature 369:324–327.

Sheets, M.D. et al., (May 1998), "Efficient construction of a large nonimmune phage antibody library: The production of high–affinity human single–chain antibodies to protein antigens," Cell Biology 95(11):6157–6162.

Shusta, E.V. et al., (Apr. 1999), "Biosynthetic polypeptide libraries," Curr. Opin. Biotechnol. 10:117–122.

Shusta, E.V. et al., (Oct. 1999), "Yeast Polypeptide Fusion Surface Display Levels Predict Thermal Stability and Soluble Secretion Efficiency," *J. Mol. Biol*. 292:949–956.

Slanetz, A.E. and Bothwell, A.L., (1991), "Heterodimeric, disulfide–linked a / b T cell receptors in solution" Eur. J. Immunol. 21:179–183.

Soo Hoo, W.F. et al., (May 1992), "Characterization of a single–chain T–cell receptor expressed in *Escherichia coli*," Proc. Natl. Acad. Sci. *USA* 89:4759–4763.

Speir, J.A. et al., (May 1998), "Structural Basis of 2C TCR Allorecognition of H–$2L^d$ Peptide Complexes," Immunity 8:553–562.

Sykuley, Y. et al., "Kinetics and Affinity of Reactions between an Antigen–Specific T Cell Receptor and Peptide–MHC Complexes" (1994), Immunity 1:15–22.

Sykulev, Y. et al., (Nov. 1994), "High–affinity reactions between antigen–specific T–cell receptors and peptides associated with allogeneic and syngeneic major histocompatibility complex class I proteins," Proc. Natl. Acad. Sci. USA 91:11487–11491.

Sykulev, Y. et al., (Dec. 1995) "The Law of mass action governs antigen–stimulated cytolytic activity of CD8+ cytotoxic T lymphocytes" Proc. Natl. Acad. Sci. USA 92:11990–11992.

Tjoa, B.and Kranz, D.M., (Jul. 1992) "Diversity of T cell receptor–alpha chain transcripts from hyperimmune alloreactive T cells." J Immunol (United States) 149(1) 253–259.

Udaka, K. et al., (1993), "A ubiquitous protein is the source of naturally occurring peptides that are recognized by a CD8+ T–cell clone" Proc. Natl. Acad. Sci. USA 90:11272–11276.

Valitutti, S.et al., "Serial triggering of many T–cell receptors by a few peptide–MHC complexes" (May 1995), Nature 375:148–151.

Ward, E.S., (1991), "Expression and Secretion of T–Cell Receptor Vα and Vβ Domains using *Escherichia coli* as a Host," Scand. J. Immunol. 34:215–220.

Ward, E.S., (1992), "Secretion of T Cell Receptor Fragments From Recombinant *Escherichia coli* Cells," J. Mol. Biol. 224:885–890.

Wedemayer, G.J.et al., "Structural Insights into the Evolution of an Antibody Combining Site" (Jun. 1997), Science 276:1665–1669.

Weidanz, J.A. et al., (Dec. 1998), "Display of functional αβ single–chain T–cell receptor molecules on the surface of bacteriophage," J. Immunol. Meth. 221:59–76.

Willcox, B.E. et al., "TCR Binding to Peptide–MHC Stabilizes a Flexible Recognition Interface" (Mar. 1999), Immunity 10:357–365.

Winter, G. et al., "Making Antibodies By Phage Display Technology" (1994) Annu. Rev. Immunol. 12:433–455.

Wittrup, D.K., "Phage on Display" (Nov. 1999), Trends in Biotech. 17(11):423–424.

Wolfe, M.S. et al., (Jan. 1998), A Substrate–Based Diffusion Ketone Selectively Inhibits Alzheimer's γ–Secretase Activity, J. Med. Chem. 41:6–9.

Al–Ramadi BK, et al., (1995)Lack of strict correlation of functional sensitation with the apparent affinity of MHC/peptide complexes for the TCR. *J. Immunol.*155: 662–673.

Bellio M, et al., (1994), The &b complementarity determining region 1 of a major histocompatibility complex (MHC) class 1–restricted T cell receptor is involved in the recognition of peptide/MHC I and superantigen/MHC complex.*J. Exp. Med.*179: 1087–1089.

Bird, RE, et al., (1988), Single–chain antigen–binding proteins. *Science*. 242: 423–426.

Boder, E.T., et al., (2000), Yeast surface display for directed evolution of protein expression, affinity, and stability. *Methods Enzymol*328, 430–444.

Brodnicki, TC., (1996), Reactivity and epitope mapping of single–chain T cell receptors with monoclonal antibodies. *Mol. Immunol.*33:253–263.

Cho, BK, et al., (1995), Characterization of a single–chain antibody to the &b–chain of the T cell receptor. *J. Biol. Chem.*270: 25819–25826.

Cochran, et al., (2000), A diverse of oligomeric class II MHC–peptide complexes for probing T–cell receptor interactions. Chemistry & Biology, vol. 7:683–696.

Corr M, et al., (1994), T cell receptor–MHC class I peptide interations: affinity, kinetics, and specificity. *Science*265: 946–949.

Engel I, et al., (1988), Site–directed mutations in the VDJ junctional region of a T cell receptor &b chain cause changes in antigenic peptide recognition. *Cell*54: 473–484.

Holler, Philip D., et al., (2001), CD8–T Cell Transfectants that Express a High Affinity T Cell Receptor Exhibit Enhanced Peptide–dependent Activation. *J. Exp. Med.* 194: 1043–1052.

Holler, et al., (2002) TCRs with high affinity for foreign pMHC show self–reactivity, *Nature Immunology*, Published online Dec. 9, 2002; doi:10.1038/ni863.

Holler, et al., (2003) Quantitative Analysis of the Contribution of TCR/pepMHC Affinity and CD8 to T Cell Activation, *Immunity*, 18:255–264.

Holler, et al., (2000) In *vitro* evolution of a T cell receptor with high affinity for peptide/MHC, *PNAS*, 97:5387–5392.

Hoogenboom, Hennie R., (1997) Designing and optimizing library selection strategies for generating high–affinity antibodies, *Tibtech*, 15:62–70.

Kasibhatla S. et al., (1993) Simultaneous involvement of all six predicted antigen binding loops of the T cell receptor in recognition of the MHC/antigenic peptide complex. *J. Immunol.* 151:3140–51.

Kieke, M.C., et al., (2001), High affinity T cell receptors from yeast display libraries block T cell activation by superantigens. J Mol Biol 307:1305–1315.

Malchiodi EL, (1995), Superantigen binding to a T cell receptor βchain of known three–dimensional structure. *J. Exp. Med.* 182:1833–1845.

Shusta, E.V., et al., (2000), Directed evolution of a stable scaffold for T–cell receptor engineering. Nat Biotechnol 18:754–759.

Wittrup, K.D., (2000), The single cell as a microplate well. Nat Biotechnol 18:1039–1040.

Yoon, ST., (1994), Both high and low avidiry antibodies to the T cell receptor can have agonist or antagonist activity. *Immunity* 1:563–569.

* cited by examiner

T2-K$^b$ cells stained with:
SA:PE
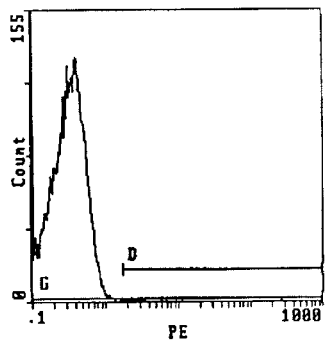
B8.24.3
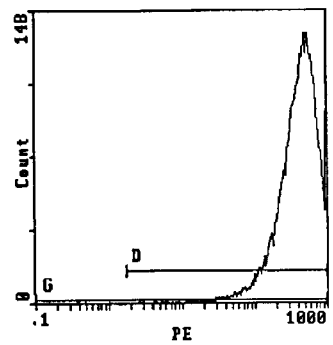
Soluble 3SQ2:biotin on T2-K$^b$ with peptide:
OVA
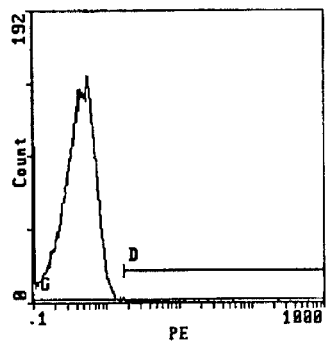
dEV8
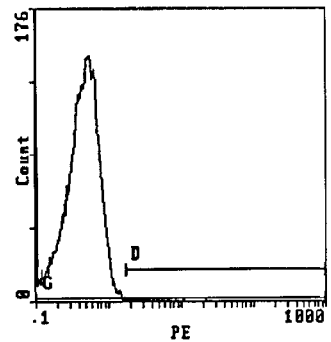
SIYR
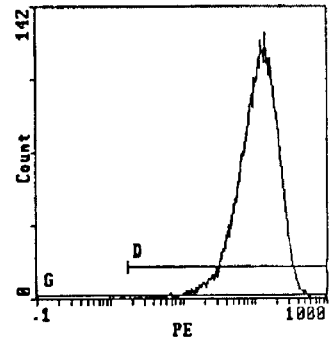
FIG. 6

| Wild Type TCR | VαCDR3 |
|---|---|
| 2C | $^{93}$SGFASAL$^{104}$ (SEQ ID NO:7) |

| Mutant TCR | VαCDR3 | Mutant TCR | VαCDR3 |
|---|---|---|---|
| q2r | SSYGNYL (SEQ ID NO:8) | q1r | SLPPPLL (SEQ ID NO:17) |
| q4r | SRRGHAL (SEQ ID NO:9) | q3r | SIPTPSL (SEQ ID NO:18) |
| q5r | SSRGTAL (SEQ ID NO:10) | qL6 | SNPPPLL (SEQ ID NO:19) |
| q6r | SHFGTRL (SEQ ID NO:11) | qL7 | SDPPPLL (SEQ ID NO:20) |
| qL1 | SMFGTRL (SEQ ID NO:12) | qL8 | SSPPPRL (SEQ ID NO:21) |
| qL2 | SHQGRYL (SEQ ID NO:13) | qL10 | SAPPPIL (SEQ ID NO:22) |
| qL3 | SYLGLRL (SEQ ID NO:14) | | |
| qL4 | SKHGIHL (SEQ ID NO:15) | | |
| qL5 | SLTGRYL (SEQ ID NO:16) | | |

FIG. 10

| | |
|---|---|
| •3SQ5 | SGTHPFL (SEQ ID NO:23) |
| SK7 | SGHLPFL (SEQ ID NO:24) |
| K5r | SDSKPFL (SEQ ID NO:25) |
| K4r | SSDRPYL (SEQ ID NO:26) |
| SK8 | SLERPYL (SEQ ID NO:27) |
| SK2 | SREAPYL (SEQ ID NO:28) |
| K3r | SLHRPAL*(SEQ ID NO:29) |
| 3SQ2 | SLHRPAL*(SEQ ID NO:30) |
| SK10 | SSNRPAL (SEQ ID NO:31) |
| K1r | STDRPSL (SEQ ID NO:32) |
| K2r | SGSRPTL (SEQ ID NO:33) |
| •SK3 | SLVTPAL (SEQ ID NO:34) |
| SK1 | SATSPAL (SEQ ID NO:35) |
| SK9 | SSINPAL (SEQ ID NO:36) |
| SK4 | SASYPSL (SEQ ID NO:37) |
| •3SQ1 | SRWTSGL (SEQ ID NO:38) |
| •Consensus | SGSRPAL (SEQ ID NO:39) |

FIG. 11

| Clone | CDR3α |
|---|---|
| 4d1 | SLTHHFL (SEQ ID NO:40) |
| 4d2 | SMTHHFL (SEQ ID NO:41) |
| 3Sd3 | SLSRPYL (SEQ ID NO:42) |
| 3dS6 | SLTRPYL (SEQ ID NO:43) |
| 3dS2 | STYRHYL (SEQ ID NO:44) |
| 3d2 | SGLARPL (SEQ ID NO:45) |
| 3SQ2 | SLHRPAL (SEQ ID NO:46) |
| 3SQ5 | SGTHPFL (SEQ ID NO:47) |

FIG. 12

| Clone | CDR3β |
|---|---|
| WT 2C | GGGGTLY (SEQ ID NO:48) |
| QB2 | GGGGVLY (SEQ ID NO:49) |
| QB4 | GLGGILY (SEQ ID NO:50) |
| QB6/8 | GQGGVLY (SEQ ID NO:51) |
| QB7 | GSGGIIY (SEQ ID NO:52) |
| QB9 | GGGGILY (SEQ ID NO:53) |

| Clone | 95 | 96 | 97 | 98 | 105 | 106 | 107 |
|---|---|---|---|---|---|---|---|
| WT 2C | GGT | GGG | GGG | GGC | ACC | TTG | TAC |
| QB2 | GGT | GGG | GGG | GGG | GTG | TTG | TAC |
| QB4 | GGT | TTG | GGG | GGG | ATC | CTC | TAC |
| QB6/8 | GGT | CAG | GGC | GGG | GTG | TTG | TAC |
| QB7 | GGT | TCG | GGG | GGG | ATC | ATC | TAC |
| QB9 | GGT | GGC | GGG | GGG | ATC | TTG | TAC |

FIG. 13

HIGH AFFINITY TCR PROTEINS AND METHODS

CROSS REFERENCE TO RELATED APPLICATIONS

This application is a continuation-in-part of U.S. application Ser. No. 09/009,388, filed Jan. 20, 1998. This application claims the benefit of U.S. Provisional Application No. 60/169,179, filed Dec. 6, 1999.

ACKNOWLEDGMENT OF FEDERAL RESEARCH SUPPORT

This invention was made with Government support under Contract No.PHS-5-R01-GM55767-03 awarded by the National Institutes of Health (NIH). The Government has certain rights in this invention.

BACKGROUND OF THE INVENTION

The field of the present invention is molecular biology, in particular, as it is related to combinatorial libraries of immune cell receptors displayed on the cell surface of a recombinant host cell. More specifically, the present invention relates to a library of high affinity T cell receptor proteins displayed on the surfaces of recombinant yeast cells, to soluble high affinity TCR receptor proteins, to high affinity TCR proteins selected for high affinity binding to particular peptide/MHC pairs, to high affinity TCR proteins selected for binding to a particular antigen in the absence of an MHC determinant, and to the use of the selected high affinity TCR derivatives in diagnostic methods and imaging assays, among other applications.

T cell receptors (TCRs) and antibodies have evolved to recognize different classes of ligands. Antibodies function as membrane-bound and soluble proteins that bind to soluble antigens, whereas in nature, TCRs function only as membrane-bound molecules that bind to cell-associated peptide/MHC antigens. All of the energy of the antibody-:antigen interaction focuses on the foreign antigen, whereas a substantial fraction of the energy of the TCR peptide/MHC interaction seems to be directed at the self-MHC molecule [Manning et al. (1998) *Immunity* 8:413:425]. In addition, antibodies can have ligand-binding affinities that are orders of magnitude higher than those of TCRs, largely because of the processes of somatic mutation and affinity maturation. In their normal cellular context, TCRs do not undergo somatic mutation, and the processes of thymic selection seem to operate by maintaining a narrow window of affinities [Alam et al. (1996) *Nature* 381:616–620]. The association of TCRs at the cell surface with the accessory molecules CD4 or CD8 also may influence the functional affinity of TCRs [Garcia et al. (1996) *Nature* 384:577–581]. Despite these differences, the three-dimensional structures of the two proteins are remarkably similar, with the hypervariable regions forming loops on a single face of the molecule that contacts the antigen.

Based on their structural similarities, it is somewhat surprising that there have been significant differences in the success of producing soluble and surface-displayed forms of the extracellular domains of TCRs and antibodies in heterologous expression systems. Many antibodies have now been expressed at high yield and solubility as either intact or Fab-fragment forms or as single-chain (sc) fragment-variable (Fv) proteins. In addition, there are numerous antigen-binding Fv fragments that have been isolated de novo and/or improved through the use of phage-display technology and, more recently, with yeast-display technology [Boder and Wittrup (1997) *Nat. Biotechnol.* 15:553–557; Kieke et al. (1997) *Prot. Eng.* 10:1303–1310]. These expression systems for antibody fragments have been key in structural studies and in the design of diagnostic and therapeutic antibodies.

In contrast, the three-dimensional structures of a few TCR molecules were determined only after considerable effort on the expression of soluble, properly folded TCRs [Bentley and Mariuzza (1996) *Ann. Rev. Immunol.* 14:563–590]. One of the difficulties in exploring the basis of differences between Fab and TCR has been that the extensive sequence diversity in antibody and TCR variable (V) regions complicates efforts to discern what features of the V regions are important for functions other than antigen binding (e.g., V region pairing and association kinetics, stability, and folding). There have been relatively few studies that have compared the V regions of TCRs and antibodies in terms of these properties.

Nevertheless, the TCR from the mouse T cell clone 2C has now been expressed as an sc $V_\alpha V_\beta$(scTCR) in *Escherichia coli* [Soo Hoo et al. (1992) *Proc. Natl. Acad. Sci. USA* 89:4759–4763], as a lipid-linked $V_\alpha C_\alpha V_\beta C_\beta$ dimer from myeloma cells [Slanetz and Bothwell (1991) *Eur. J. Immunol.* 21:179–183], and as a secreted $V_\alpha C_\alpha V_{\beta C\beta}$ dimer from insect cells [Garcia et al. (1996) *Science* 274:209–219]. The 2C scTCR had relatively low solubility compared with most scFv, although its solubility is increased about 10-fold by fusion at the amino terminus to thioredoxin [Schodin et al. (1996) *Molec. Immunol.* 33:819–829]. The difficulty in generating soluble, properly folded $V_\alpha V_\beta$ domains has extended to other TCRs [Udaka et al. (1993) supra; Sykulev et al. (1994) supra; Manning et al. (1998) supra]. The molecular explanation for the apparent differences between TCR and Fv in either solubility or surface-display capability has not been explored adequately. It has been shown that the 2C scTCR can be expressed in a yeast surface-display system after the selection, from a random library, of specific single-site mutations at the $V_\alpha/V_\beta$ interface or in a region of the $V_\beta$ framework suspected to interact with the $CD3_\epsilon$ signal-transduction sub-unit. These mutations, several of which are found naturally in antibody V regions, reflect the significance of these positions in the TCR and provide a basis for further engineering of TCR-binding properties.

SUMMARY OF THE INVENTION

The invention provides a combinatorial library of immune T cell receptor polypeptides displayed on the surfaces of recombinant host cells, for example, yeast cells, desirably *Saccharomyces cerevisiae*. From such a library can be isolated high affinity TCR polypeptides (those that exhibit higher affinity than wild type for the cognate ligand: a complex of peptide bound to a protein of the major histocompatibility complex, pMHC). Desirably, the affinity of the TCR peptide for the pMHC is reflected in a dissociation constant of from about $10^7$ to about $10^{10}$, e.g., as measured by methods known to the art. A DNA library comprising nucleic acids encoding soluble high affinity TCRs, wherein said TCRs are made by the method of mutagenizing a TCR to create mutant TCR coding sequences; transforming DNA comprising the mutant TCR coding sequences for mutant TCRs into yeast cells; inducing expression of the mutant TCR coding sequences such that the mutant TCRs are displayed on the surface of yeast cells; contacting the yeast cells with a fluorescent label which binds to the peptide/MHC ligand to produce selected yeast cells; and isolating the yeast cells showing the highest fluorescence is provided.

Also provided is a library of T cell receptor proteins displayed on the surface of yeast cells which have higher affinity for the peptide/MHC ligand than the wild type T cell receptor protein, wherein said library is formed by mutagenizing a T cell receptor protein coding sequence to generate a variegated population of mutants of the T cell receptor protein coding sequence; transforming the T cell receptor mutant coding sequence into yeast cells; inducing expression of the T cell receptor mutant coding sequence on the surface of yeast cells; and selecting those cells expressing T cell receptor mutants that have higher affinity for the peptide/MHC ligand than the wild type T cell receptor protein.

The present invention further provides TCR proteins (in cell-bound or in soluble form) that exhibit high affinity binding for the cognate ligand. In the present invention the ligand bound by the TCR protein can be a peptide/MHC complex or because of the selection process, desirably an iterated selection process, it can be a ligand which does not include an MHC component, such as a superantigen. This ligand can be a peptide, a protein, a carbohydrate moiety, or a lipid moiety, among others. These soluble high affinity TCRs may be made by the method comprising: mutagenizing a TCR to create mutant TCR coding sequences; transforming DNA comprising the mutant TCR coding sequences for mutant TCRs into yeast cells; inducing expression of the mutant TCR coding sequences such that the mutant TCRs are displayed on the surface of yeast cells; contacting the yeast cells with a fluorescent label which binds to the peptide/MHC ligand to produce selected yeast cells; and isolating the yeast cells showing the highest fluorescence. The soluble high affinity TCRs are preferably isolated by yeast display.

The present invention further provides methods for detecting the cognate ligand of a high affinity TCR protein, said methods comprising the step of binding the high affinity TCR protein with the cognate ligand, where the high affinity TCR protein is detectably labeled or where there is a secondary detectable protein added, such as an antibody specific for the TCR in a region other than the region which binds the cognate ligand. A preferred method for using high affinity TCRs to identify ligands comprises: labeling high affinity TCRs with a detectable label; contacting said labeled TCRs with ligands; identifying the ligand with which the labeled TCR is bound. Preferably the ligands are those peptide/MHC ligands to which the TCR binds with higher affinity than the wild type TCR. Methods of identifying the ligand are known to one of ordinary skill in the art. Suitable labels allowing for detection of the TCR protein, directly or indirectly, include but are not limited to fluorescent compounds, chemiluminescent compounds, radioisotopes, chromophores, and others.

The high affinity TCR protein can be used in the laboratory as a tool for qualitative and quantitative measurements of a target ligand, in medical, veterinary or plant diagnostic setting or for tissue or plant material identification. Similarly, the high affinity TCRs of the present invention can be used as reagents for detecting and/or quantitating a target material or ligand. Also provided is a method of using high affinity TCRs to bind to a selected peptide/MHC ligand comprising: labeling said high affinity TCRs with a label that binds to the selected peptide/MHC ligand; contacting said labeled high affinity TCRs with cells containing MHC molecules. The high affinity protein of the present invention, where it specifically binds to a tumor cell antigen with high affinity and specificity can be used in diagnostic tests for the particular type of cancer or it can be used in an organism in imaging tests to locate and/or estimate size and number of tumors in an organism, preferably a mammal, and also preferably a human. Methods provided for using high affinity TCRs that bind to pMHCs for diagnostic tests comprise: labeling the high affinity TCR with a detectable label; contacting said high affinity TCR with cells containing the ligand to which the high affinity TCR has high affinity for; and detecting the label. In the method, the label may be chosen to bind to specific peptide/MHC ligands, whereby cells that express specific peptide/MHC ligands are targeted. Preferred methods for using high affinity TCRs as diagnostic probes for specific peptide/MHC molecules on surfaces of cells comprise: labeling high affinity TCRs with a detectable label that binds to specific peptide/MHC ligands; contacting said TCRs with cells; and detecting said label. The detectable label chosen for use depends on the particular use, and the choice of a suitable label is well within the ordinary skill of one in the relevant art. In general, the TCR proteins selected for high affinity binding to a ligand of interest can be used in methods in which antibodies specific for the ligand can be used, with procedural modifications made for the TCR vs. antibody protein, such modifications being known in the art.

The high affinity TCR, desirably a soluble single chain (sc) TCR, can be used to block autoimmune destruction of cells or tissues in autoimmune disease, where the site recognized by the cytotoxic lymphocytes on the surface of the target cell is the same as the site bound by the high affinity TCR. Preferred methods for blocking autoimmune destruction of cells comprise contacting TCRs with high affinity for the site recognized by the T lymphocytes on the surface of a target cell with cells, whereby the autoimmune destruction of cells is blocked.

A soluble, high affinity scTCR can be coupled to a therapeutic compound (e.g., an anticancer compound, a therapeutic radionuclide or a cytoxic protein) where the cognate ligand of the sc TCR is a neoplastic cell surface marker. Alternatively, the binding specificity of the high affinity soluble sc TCR can be a pathogen infected target cell (such as virus-, bacteria- or protozoan-infected) and a toxic molecule can be coupled so that the target cell can be eliminated without further replication of the infective agent. Provided methods of using high affinity TCRs to inactivate pathogens comprise: binding a molecule which is toxic to the pathogen to the high affinity TCR; and contacting said TCR with cells that express said pathogen. "Toxic" means that the pathogen prevents or inhibits replication of the pathogen.

Also provided are methods for using high affinity TCRs to treat disease comprising: coupling a TCR having a high affinity for a neoplastic cell surface marker with a therapeutic compound; and contacting said TCR with cells. Any therapeutic compound that is useful in slowing the progress of the disease that can be coupled with the TCR may be used. Methods of coupling the therapeutic compound with the TCR are known in the art.

Also provided is a method for cloning the gene for a high affinity TCR mutant into a system that allows expression of the mutant on the surface of T cells comprising: mutating TCRs to create high affinity TCR mutants; cloning said TCR mutants into a vector; transfecting the vector into T cells; expressing the high affinity TCR mutant on the surface of T cells. This method may further comprise: selecting those T cells that are activated to a greater extent than other T cells by a peptide/MHC ligand. The transfected/infected T cells may be used for recognition of selected peptide-bearing MHC cells. These transfected/infected T cells are useful in treating disease in patients where T cells from a patient are removed and transformed with the vector that expresses the high affinity TCR mutants and returned to the patient where they are activated to a greater extent by a peptide/MHC ligand than the patient's wild type T cells.

A soluble, high affinity TCR molecule can be used in place of an antibody or single chain antibody for most applications, as will be readily apparent to one of skill in the relevant arts.

BRIEF DESCRIPTION OF THE DRAWINGS

FIG. 4A: Flow cytometry histograms of T2-$L^d$ cells loaded with QL9 (unshaded), p2Ca (light shade), or MCMV (SEQ ID NO:1) (dark shade) and stained with qL2 scTCR/biotin. FIG. 4B: Mean fluorescent units (MFU) of T2-$L^d$ cells loaded with QL9, p2Ca, or MCMV (SEQ ID NO:1) and stained with either secondary SA-PE only, T7 scTCR/biotin+SA-PE, or qL2 scTCR/biotin+SA-PE. FIG. 4C: A soluble, high affinity form of mutant qL2 expressed from insect cells can detect very low concentrations of a peptide-MHC complex. Ld complexes were up-regulated on the surface of T2-Ld cells (3×10$^6$/ml) by incubation with various concentrations of QL9 peptide at 37° C. for 1.5 hr. Approximately 2×10$^5$ cells were stained for 30 min on ice with TCRs derived from transfected *Drosophila melanogaster* (insect) SC2 cells (Garcia, K. C., et al. (1997) *Proc Natl Acad Sci USA* 94(25), 13838–13843). Cells were then washed and stained with biotin-labeled anti-Vb IgG (F23.1) followed by streptavidin-PE and analyzed by flow cytometry.

FIG. 6: T2-$K^b$ tumor cells were incubated with specific peptides (OVA, dEV8 or SIYR (SEQ ID NO:2)) and analyzed by flow cytometry staining with biotinylated soluble scTCR, 3SQ2 followed by streptavidin-PE. As a positive control for the presence of $K^b$, T2-$K^b$ cells were stained with biotinylated antibody B8.24.3, which recognizes $K^b$ irrespective of the bound peptide.

FIG. 10: Structure and sequences of the 2C TCR CDR3α. Alignment of amino acid sequences (SEQ ID NO: 8–22) of mutant scTCRs isolated by yeast display and selection with QL9/$L^d$. Display plasmids were isolated from yeast clones after selection and sequenced to determine CDR3α sequences. Mutants m1, m2, m3, m4, m10 and m11 were isolated after the third round of sorting. All other mutants were isolated after the fourth round of sorting.

FIG. 11: SIYR/$K^b$ Binders (3SQ2, 3SQ5): CDR3α Sequences (SEQ ID NO: 23–39).

FIG. 12: Alignment of VαCDR3 Mutant Sequences (SEQ ID NO: 40–47) with High Affinity of dEV8/$K^b$ (4d1, 4d2, 3Sd3, 3dS6, 3dS2, 3d2) and SIYR/$K^b$.

FIG. 13: Alignment of VβCDR3 Sequences of Mutant scTCRs (SEQ ID NO: 48–53) Selected for High Affinity for QL9/$L^D$ from a CDR3α Yeast Library. All have qL2 CDR3α (SHQGRYL (SEQ ID NO:13)). QB/5=wt; QB3 not sequenced.

DETAILED DESCRIPTION OF THE PREFERRED EMBODIMENTS

Figure 1:
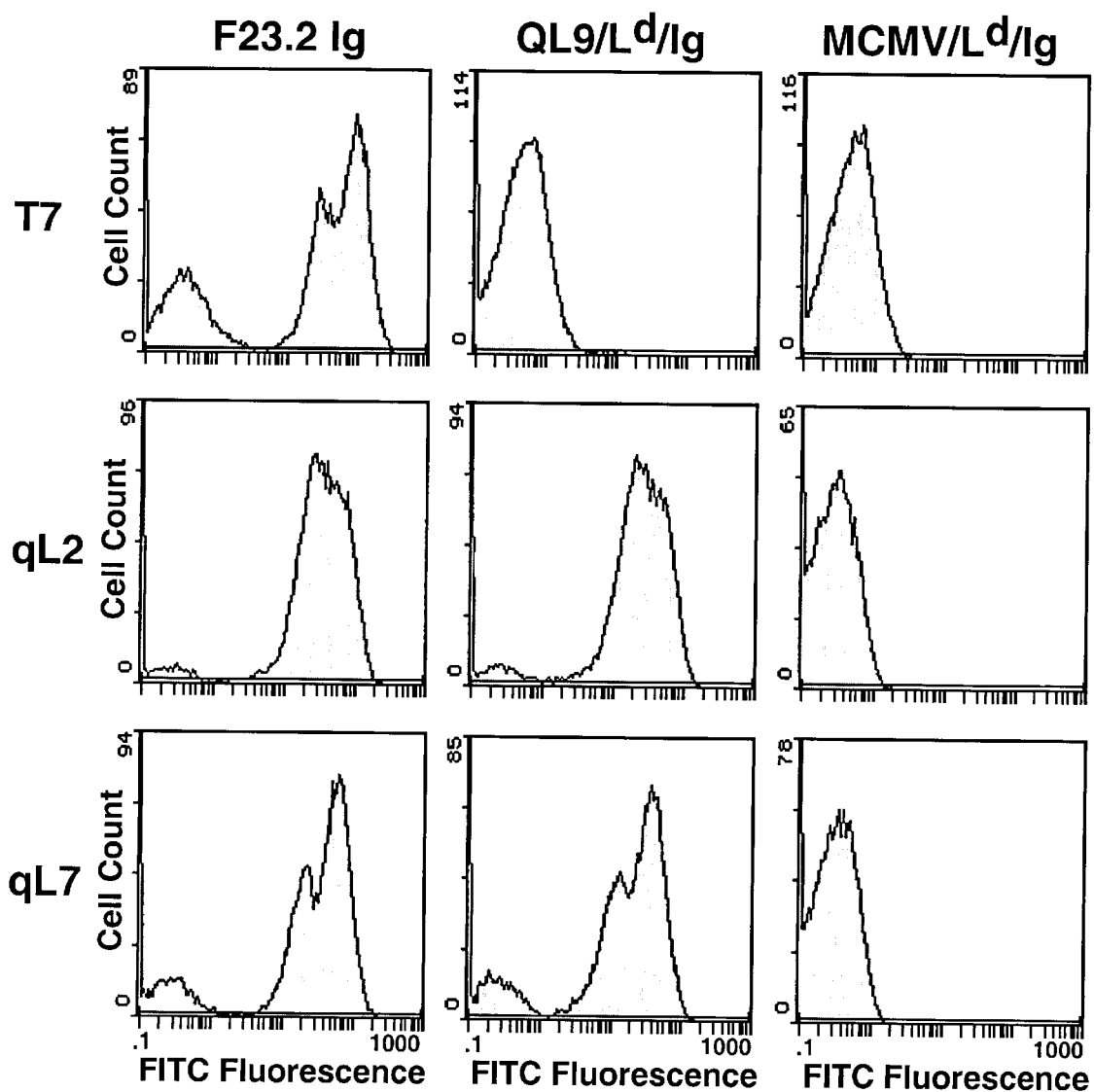
FIG. 1: Flow cytometric analysis of yeast cells that express wild-type and mutant 2C TCR on their surfaces. Yeast cells displaying wild-type (T7) and mutant (qL2, qL7) scTCR were stained with anti-Vβ8 antibody F23.2 (120 nM), the specific alloantigenic peptide-MHC, QL9/$L^d$/Ig (40 nM), or a null peptide MCMV(SEQ ID NO:1)$L^d$/Ig (40 nM). Binding was detected by FITC-conjugated goat anti-mouse IgG F(ab')$_2$ and analyzed by flow cytometry. The negative population (e.g. seen with F23.2 staining) has been observed for all yeast displayed-proteins and is thought to be due to cells at a stage of growth or induction that are incapable of expressing surface fusion protein (Kieke et al. (1999) *Proc. Natl. Acad. Sci. USA* 96:5651–5656; Boder and Wittrup (1997) *Nat. Biotech.* 15:553–557; Kieke et al. (1997) *Protein Engineering* 10:1303–1310).

In order to provide a clear and consistent understanding of the specification and claims, including the scope to be given to such terms, the following definitions are provided.

A coding sequence is the part of a gene or cDNA which codes for the amino acid sequence of a protein, or for a functional RNA such as a tRNA or rRNA.

Complement or complementary sequence means a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'.

Downstream means on the 3' side of any site in DNA or RNA.

Expression refers to the transcription of a gene into structural RNA (rRNA, tRNA) or messenger RNA (mRNA) and subsequent translation of a mRNA into a protein.

An amino acid sequence that is functionally equivalent to a specifically exemplified TCR sequence is an amino acid sequence that has been modified by single or multiple amino acid substitutions, by addition and/or deletion of amino acids, or where one or more amino acids have been chemically modified, but which nevertheless retains the binding specificity and high affinity binding activity of a cell-bound or a soluble TCR protein of the present invention. Functionally equivalent nucleotide sequences are those that encode polypeptides having substantially the same biological activity as a specifically exemplified cell-bound or soluble TCR protein. In the context of the present invention, a soluble TCR protein lacks the portions of a native cell-bound TCR and is stable in solution (i.e., it does not generally aggregate in solution when handled as described herein and under standard conditions for protein solutions).

Two nucleic acid sequences are heterologous to one another if the sequences are derived from separate organisms, whether or not such organisms are of different species, as long as the sequences do not naturally occur together in the same arrangement in the same organism.

Homology refers to the extent of identity between two nucleotide or amino acid sequences.

Isolated means altered by the hand of man from the natural state. If an "isolated" composition or substance occurs in nature, it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein.

A linker region is an amino acid sequence that operably links two functional or structural domains of a protein.

A nucleic acid construct is a nucleic acid molecule which is isolated from a naturally occurring gene or which has been modified to contain segments of nucleic acid which are combined and juxtaposed in a manner which would not otherwise exist in nature.

Nucleic acid molecule means a single- or double-stranded linear polynucleotide containing either deoxyribonucleotides or ribonucleotides that are linked by 3'-5'-phosphodiester bonds.

Two DNA sequences are operably linked if the nature of the linkage does not interfere with the ability of the sequences to effect their normal functions relative to each other. For instance, a promoter region would be operably linked to a coding sequence if the promoter were capable of effecting transcription of that coding sequence.

A polypeptide is a linear polymer of amino acids that are linked by peptide bonds.

Promoter means a cis-acting DNA sequence, generally 80–120 base pairs long and located upstream of the initiation site of a gene, to which RNA polymerase may bind and initiate correct transcription. There can be associated additional transcription regulatory sequences which provide on/off regulation of transcription and/or which enhance (increase) expression of the downstream coding sequence.

A recombinant nucleic acid molecule, for instance a recombinant DNA molecule, is a novel nucleic acid sequence formed in vitro through the ligation of two or more nonhomologous DNA molecules (for example a recombinant plasmid containing one or more inserts of foreign DNA cloned into at least one cloning site).

Transformation means the directed modification of the genome of a cell by the external application of purified recombinant DNA from another cell of different genotype, leading to its uptake and integration into the subject cell's genome. In bacteria, the recombinant DNA is not typically integrated into the bacterial chromosome, but instead replicates autonomously as a plasmid.

Upstream means on the 5' side of any site in DNA or RNA.

A vector is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

High affinity T cell receptor (TCR) means an engineered TCR with stronger binding to a target ligand than the wild type TCR.

T cells recognize a foreign peptide bound to the MHC product through the αβ heterodimeric T cell receptor (TCR). The TCR repertoire has extensive diversity created by the same gene rearrangement mechanisms used in antibody heavy and light chain genes [Tonegawa, S. (1988) *Biosci. Rep.* 8:3–26]. Most of the diversity is generated at the junctions of variable (V) and joining (J) (or diversity, D) regions that encode the complementarity determining region 3 (CDR3) of the α and β chains [Davis and Bjorkman (1988) *Nature* 334:395–402]. However, TCRs do not undergo somatic point mutations as do antibodies and, perhaps not coincidentally, TCRs also do not undergo the same extent of affinity maturation as antibodies. TCRs as they occur in nature appear to have affinities that range from $10^5$ to $10^6$ $M^{-1}$ whereas antibodies typically have affinities that range from $10^5$ to $10^9$ $M^{-1}$ [Davis et al. (1998) *Annu. Rev. Immunol.* 16:523–544; Eisen et al. (1996) *Adv. Protein Chem.* 49:1–56]. While the absence of somatic mutation in TCRs may be associated with lower affinities, it has also been argued that there is not a selective advantage for a TCR to have higher affinity. In fact, the serial-triggering [Valitutti et al. (1995) *Nature* 375:148–151] and kinetic proofreading [Rabinowitz et al. (1996) *Proc. Natl. Acad. Sci. USA* 93:1401–1405] models of T cell activation both suggest that longer off-rates (associated with higher affinity) would be detrimental to the signaling process. It is also possible that higher affinity TCRs might not maintain the peptide specificity required for T cell responses. For example, peptides bound within the MHC groove display limited accessible surface [Bjorkman, P. J. (1997) Cell 89:167–170], which may in turn limit the amount of energy that can be generated in the interaction. On the other hand, raising the affinity of a TCR by directing the energy toward the MHC helices would presumably lead to thymic deletion during negative selection [Bevan, M. J. (1997) Immunity 7:175–178].

We show that there is not an inherent structural property or genetic limitation on higher affinity of T cell receptor proteins. Higher affinity TCR variants were generated in the absence of in vivo selection pressures by using yeast display combinatorial technology and TCR mutants (e.g., Vα and Vβ CDR3 mutants). Mutants selected for relatively strong binding to the target ligand (a particular p/MHC complex) can have greater than 100-fold higher affinity, i.e., a $K_d$ of about 10 nM for the p/MHC, and these mutants retained a high degree of peptide specificity. A strong preference for TCR proteins with conserved CDR3 motifs that were rich in proline or glycine were also evident. A soluble monomeric form of a high affinity TCR was capable of directly detecting p/MHC complexes on antigen-presenting cells. These findings prove that affinity maturation of TCRs is possible, at least in vitro. Thus, engineered TCR proteins can be used for targeting specific ligands, including particular p/MHC complexes and peptides, proteins or other ligands in the absence of a MHC component.

To examine if it is possible to generate higher affinity TCR that retain peptide specificity, we subjected a characterized TCR to a process of directed in vitro evolution. Phage display technology [Clackson et al. (1991) Nature 352:624–628] has not yet proven successful in the engineering of single-chain TCRs (scTCRs, Vβ-linker-Vα), despite the extensive structural similarity between antibody and TCR V regions. However, we recently showed that a scTCR could be displayed on the surface of yeast [Kieke et al. (1999) Proc. Natl. Acad. Sci. USA 96:5651–5656], in a system that has proven successful in antibody engineering [Boder and Wittrup (1997) supra; Kieke et al. (1997) supra]. A temperature-stabilized variant (called T7) [Shusta et al. (1999) J. Mol. Biol. 292:949–956] of the scTCR from the CTL clone 2C was used in the present study. CTL clone 2C recognizes the alloantigen $L^d$ with a bound octamer peptide called p2Ca, derived from the enzyme 2-oxoglutarate dehydrogenase [Udaka et al. (1993) Proc. Natl. Acad. Sci. USA 90:11272–11276]. The nonameric variant QL9 is also recognized by CTL 2C, but with 10-fold higher affinity by the 2C TCR [Sykulev et al. (1994) Proc. Natl. Acad. Sci. USA 91:11487–11491]. Alanine scanning mutagenesis shows that the CDR3α loop contributed minimal energy to the binding interaction [Manning (1998) supra], even though structural studies have shown that CDR3α of the 2C TCR is near the peptide and it undergoes a conformational change in order to accommodate the pMHC complex [Garcia (1998) Science 279:1166–1172]. Thus, we focused our mutagenesis efforts on the five residues that form the tip of CDR3α.

A library of $10^5$ independent TCR-CDR3α yeast mutants was subjected to selection by flow cytometry with a fluorescently-labeled QL9/$L^d$ ligand [Dal Porto et al. (1993) Proc. Natl. Acad. Sci. USA 90:6671–6675]. After four rounds of sorting and growth, fifteen different yeast colonies were examined for their ability to bind the ligand, in comparison to the scTCR variant T7, which bears the wt CRD3α sequence (FIG. 1). The anti-Vβ8.2 antibody F23.2 which recognizes residues in the CDR1 and CDR2 regions of the protein was used as a control to show that wt scTCR-T7 and scTCR mutants (qL2 and qL7 in FIG. 1 and others) each had approximately equivalent surface levels of the scTCR (FIG. 1). In contrast, the soluble QL9/$L^d$ ligand bound very well to each mutant yeast clone but not to wt scTCR-T7. The MCMV (SEQ ID NO:1)/$L^d$ complex, which is not recognized by CTL clone 2C, did not bind to the scTCR mutants or to the wt scTCR-T7, indicating that the scTCR mutants retained peptide specificity. The relative affinities of the mutant TCR also appeared to vary among clones, based on differences in signals observed with the QL9/$L^d$ ligand at constant concentrations.

CDR3α sequences of the fifteen mutants all differed from the starting 2C TCR sequence FIG. 10. Comparison by a BLAST alignment algorithm aligned the sequences into two motifs. One motif contained glycine in the middle of the 5 residue stretch whereas the other motif contained three tandem prolines. Evidence that all three prolines are important in generating the highest affinity site is suggested by results with mutant q3r. Mutant q3r contained only two of the three prolines and exhibited reduced binding compared to the triple-proline mutants. The glycine-containing mutants appeared to have preferences for positive-charged residues among the two residues to the carboxy side (7/9) and aromatic and/or positive-charged residues among the two residues to the amino side (4/9 and 5/9). Without wishing to be bound by theory, it is believed that the selection for a glycine residue at position 102 in the motif indicates that the CDR3α loop requires conformational flexibility around this residue in order to achieve increased affinity. This is consistent with the large (6 Å) conformational difference observed between the CDR3α loops of the liganded and unliganded TCR [Garcia et al. (1998) supra]. It is also interesting to note that glycine is the most common residue at the V(D)J junctions of antibodies and that the presence of a glycine has recently been associated with increased affinity in the response to the (4-hydroxy-3-nitrophenyl) acetyl hapten [Furukawa et al. (1999) Immunity 11:329–338].

In contrast to the isolates that contain glycine, the selection for a proline-rich sequence at the tip of the CDR3α loop is believed, without wishing to be bound by any particular theory, to indicate that these TCR molecules exhibit a more rigid conformation that confers higher affinity. The X-ray crystallographic structures of a germ line antibody of low affinity compared to its affinity-matured derivative showed that the high affinity state may have been due to the stabilization of the antibody in a configuration that accommodated the hapten [Wedemayer et al. (1997) Science 276:1665–1669]. Similarly, the NMR solution structure of a scTCR that may be analogous to the germline antibody showed that the CDR3α and β loops both exhibited significant mobility [Hare et al. (1999) Nat. Struct. Biol. 6:574–581]. Recent thermodynamic studies of TCR:pMHC interactions have also suggested the importance of conformational changes in binding [Willcox et al. (1999) Immunity 10:357–365; Boniface et al. (1999) Proc. Natl. Acad. Sci. USA 96:11446–11451]. Structural and thermodynamic studies of the TCR mutants discussed herein allowed us to examine if the two CDR3α motifs (Gly versus Pro-rich) differ in the mechanism by which they confer higher affinity.

Figure 2:
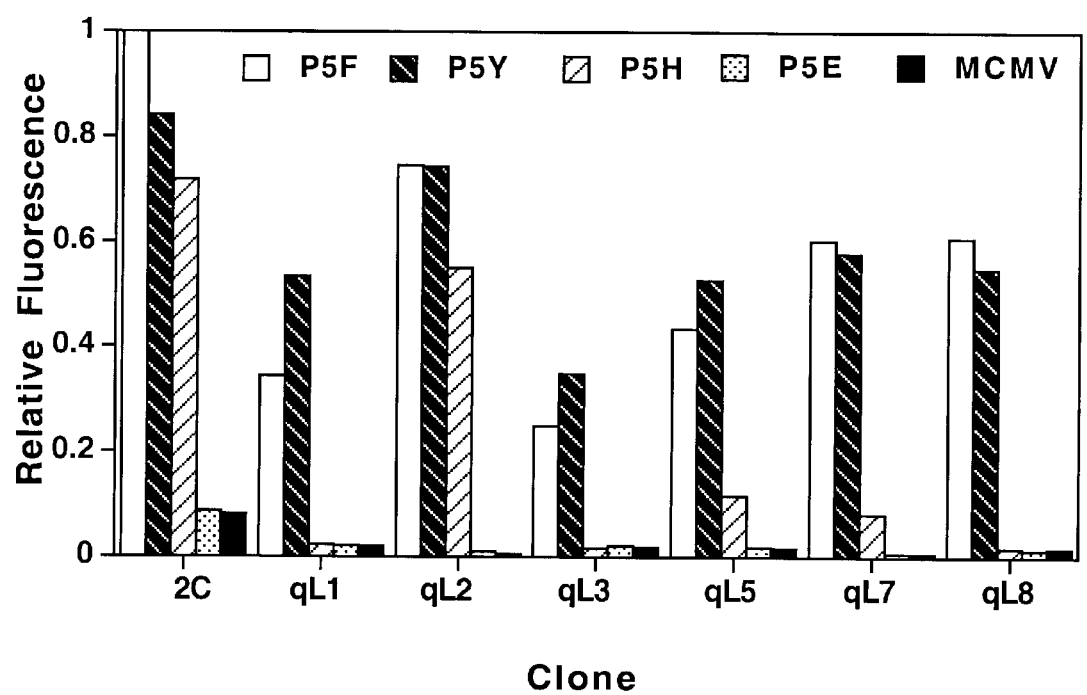
FIG. 2: Fine specificity analysis of mutant scTCR binding to different QL9 variant peptides bound to $L^d$. The original T cell clone 2C and various yeast clones were analyzed by flow cytometry for binding to $L^d$/Ig dimers loaded with wild type QL9 (P5F), position 5 variants of QL9 (P5Y, P5H, P5E) or MCMV (SEQ ID NO:1). Binding was detected with FITC-labeled goat anti-mouse IgG. Relative fluorescence was measured by two different approaches. For T cell clone 2C, the binding of the various peptide/$L^d$ Ig dimers was adjusted relative to the QL9/$L^d$ staining (MFU$_{pMHC}$/MFU$_{QL9-Ld}$). For yeast cells, the binding of each peptide/$L^d$ dimer was adjusted relative to binding by the anti-Vβ8 antibody F23.2 (MFU$_{pMHC}$/MFU$_{F23.2}$). The latter allowed different mutants to be compared relative to each other for binding to the wild type QL9/$L^d$.

Although the scTCR mutants did not bind the null (irrelevant) peptide/$L^d$ complex MCMV (SEQ ID NO:1)/$L^d$, it remained possible that the increase in affinity was accompanied by a change in fine specificity. To examine this question, we used QL9 position 5 (Phe) peptide variants which have been shown previously to exhibit significant differences in their binding affinity for the wt 2C TCR [Schlueter (1996) J. Immunol. 157:4478–4485]. The binding of these pMHC to various TCR mutants on the yeast surface and to clone 2C was measured by flow cytometry. As shown in FIG. 2, the native TCR on 2C is capable of binding QL9 variants that contain either tyrosine or histidine at position 5 but not those containing glutamic acid. Each of the higher affinity TCR mutants retained the ability to recognize the conservative tyrosine-substituted peptide, and they were likewise incapable of recognizing the glutamic acid-substituted peptide. However, several of the TCR mutants (qL2, qL5, and qL7) bound to the histidine-substituted peptide (albeit to different extents) whereas other mutants (qL 1, qL3, and qL8) did not bind this peptide (within the detection limits of this assay). Thus, the CDR3α loop can influence the peptide fine specificity of recognition, but it is not the only region of the TCR involved. The effect on peptide specificity could be through direct interaction of CDR3α residues with the variant peptide, as suggested from earlier studies involving CDR3-directed selections [Sant' Angelo et al. (1996) *Immunity* 4:367–376; Jorgensen et al. (1992) *Nature* 355:224–230]. Alternatively, binding energy may be directed at peptide-induced changes in the $L^d$ molecule itself. The latter possibility is perhaps more likely in the case of the 2C TCR:QL9/$L^d$ interaction, as position 5 of QL9 has been predicted to point toward the $L^d$ groove [Schlueter et al. (1996) supra; Speir et al. (1998) *Immunity* 8:553–562]. The fine-specificity analysis also shows that it is possible to engineer TCR with increased, or at least altered, specificity for cognate peptides. Thus, directed evolution of only a short region (CDR3α) of a single TCR allows the isolation of many TCR variants with desirable peptide-binding specificities and/or increased binding affinities.

Figure 3:
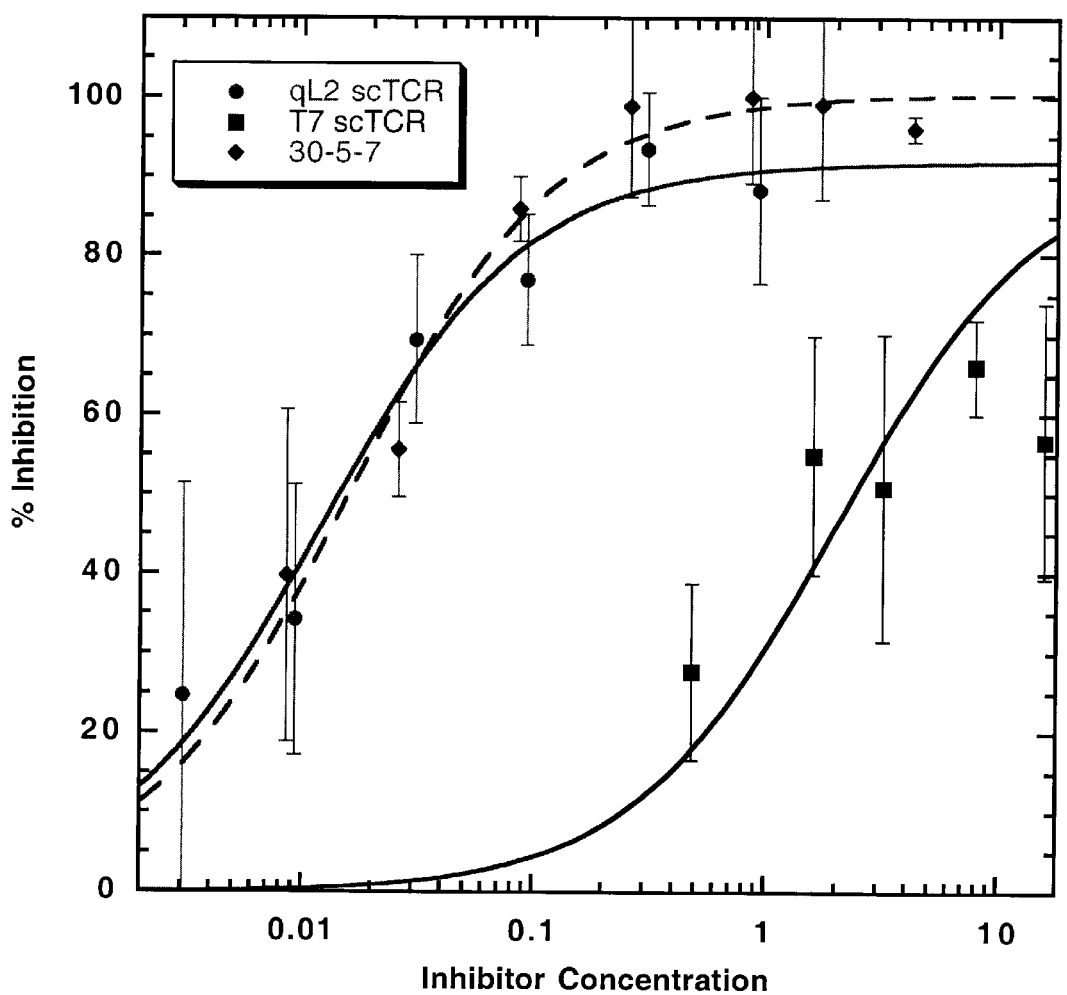
FIG. 3: QL9/$L^d$ binding by soluble scTCRs. T2-$L^d$ cells loaded with QL9 were incubated with $^{125}$I-labeled anti-$L^d$ Fab fragments (30-5-7) and various concentrations of unlabeled Fab (♦), scTCR-T7 (■), or mutant scTCR-qL2 (●). Bound and unbound $^{125}$I 30-5-7 Fab fragments were separated by centrifugation through olive oil/dibutyl phthalate. Binding of $^{125}$I-labeled anti-$L^d$ Fab fragments to T2-$L^d$ cells loaded with the control peptide MCMV (SEQ ID NO:1) was not inhibited even at the highest concentrations of scTCRs (data not shown).

In order to determine the magnitude of the affinity increases associated with a selected CDR3α mutant, the wild type T7 scTCR and the qL2 scTCR were expressed as soluble forms in a yeast secretion system. Purified scTCR preparations were compared for their ability to block the binding of a $^{125}$I-labeled anti-$L^d$ Fab fragments to QL9 or MCMV (SEQ ID NO:1) loaded onto $L^d$ on the surface of T2-$L^d$ cells [Manning (1998) supra; Sykulev et al. (1994) *Immunity* 1:15–22]. As expected, neither T7 nor qL2 scTCR were capable of inhibiting the binding of $^{125}$I-Fab fragments to T2-$L^d$ cells upregulated with the MCMV (SEQ ID NO:1) peptide. However, both T7 and qL2 were capable of inhibiting the binding of anti-$L^d$ Fab fragments to QL9/$L^d$ (FIG. 3). The qL2 scTCR variant was as effective as unlabeled Fab fragments in inhibiting binding, whereas the T7 scTCR was 160-fold less effective (average of 140-fold difference among four independent titrations). The $K_D$ values of the scTCR for the QL9/$L^d$ were calculated from the inhibition curves to be 1.5 µM for T7 and 9.0 nM for qL2. The value for T7 is in close agreement with the 3.2 µM $K_D$ previously reported for the 2C scTCR [Manning et al. (1999) *J. Exp. Med.* 189:461–470]. These findings show that the yeast system, combined with CDR3α-directed mutagenesis, allows selection of mutants with at least about 100-fold higher intrinsic binding affinities for a particular pMHC ligand.

Figure 4A:
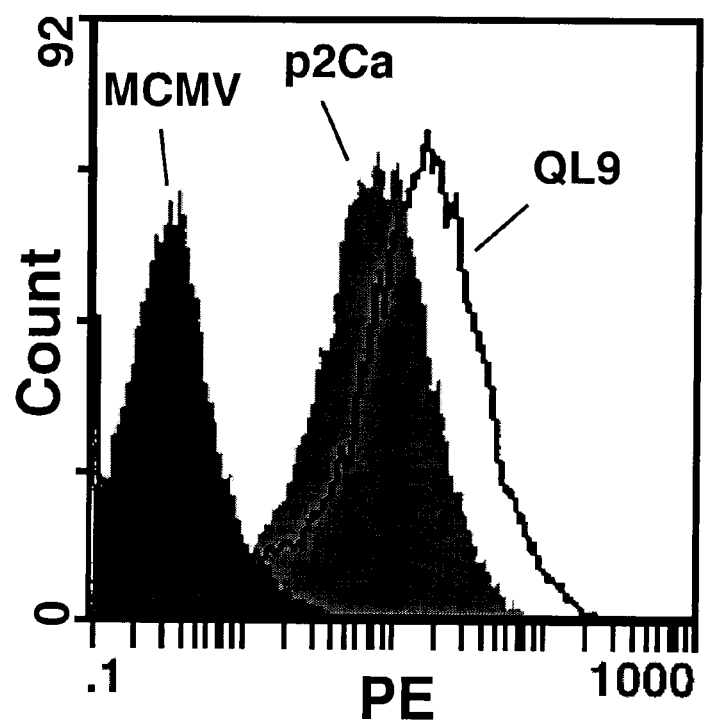
FIGS. 4A–C: Flow cytometric analysis of the binding of scTCR/biotin to cell surface peptide/MHC. Peptide-loaded T2-$L^d$ cells were incubated with biotinylated qL2 scTCR (~0.3 μM) or T7 scTCR (~1.6 μM) scTCR followed by streptavidin-PE and analyzed by flow cytometry.
Figure 4B:
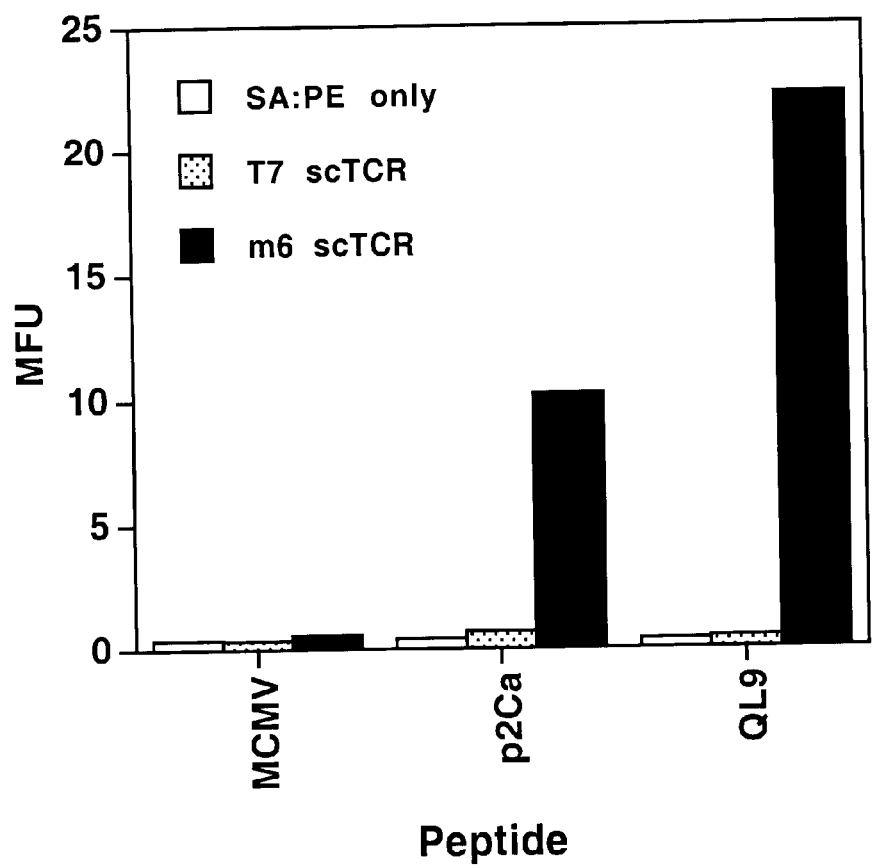
Figure 4C:
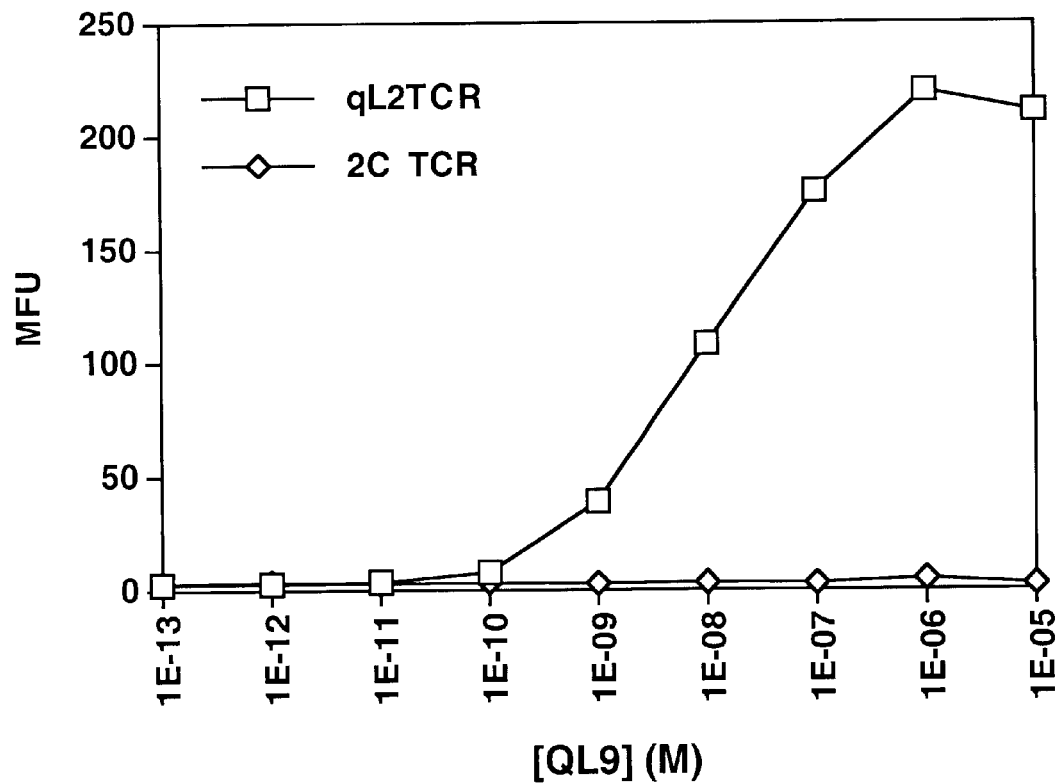

If the soluble scTCR has a high affinity for its pMHC ligand, then it is useful, like antibodies, as a specific probe for cell-surface bound antigen. To confirm this, the soluble T7 and qL2 scTCR were biotinylated, and the labeled-scTCR molecules were incubated with T2-$L^d$ cells loaded with QL9, p2Ca, or MCMV (SEQ ID NO:1). The qL2 scTCR, but not the T7 scTCR, yielded easily detectable staining of the T2 cells that had been incubated with QL9 or p2Ca (FIGS. 4A–4B). It is significant that p2Ca-upregulated cells were also readily detected by qL2 scTCR, as p2Ca is the naturally processed form of the peptide recognized by the alloreactive clone 2C and it has an even lower affinity than the QL9/$L^d$ complex for the 2C TCR [Sykulev et al. (1994) supra].

The high affinity receptors described in our study were derived by variation at the VJ junction, the same process that operates very effectively in vivo through gene rearrangements in T cells (Davis and Bjorkman (1988) *Nature* 334:395–402). The fact that we could readily isolate a diverse set of high affinity TCR in vitro indicates that there is not a genetic or structural limitation to high affinity receptors. This supports the view that inherently low affinities of TCRs found in vivo are due to a lack of selection for higher affinity and perhaps a selection for lower affinity (Sykulev et al. (1995) *Proc. Natl. Acad. Sci. USA* 92:11990–11992; Valitutti et al. (1995) *Nature* 375:148–151; Rabinowitz et al. (1996) *Proc. Natl. Acad. Sci. USA* 93:1401–1405). In this respect, the higher affinity TCRs of the present invention now provide the reagents for directly testing hypotheses about the effects of affinity on T cell responses (Davis et al. (1998) *Ann. Rev. Immunol.* 16:523–544; Sykulev et al. (1995) supra; Valitutti et al. (1995) supra; Rabinowitz et al. 1996) supra).

In summary, we have shown that T cell receptors, which represent a class of proteins as diverse as antibodies, can be engineered like antibodies to yield high affinity, antigen-specific probes. Furthermore, a soluble version of the high affinity receptor can directly detect specific peptide/MHC complexes on cells. Thus, these engineered proteins are useful as diagnostics, for tumor cells, for example. Soluble derivatives of the high affinity TCRs are useful or can be further engineered as high affinity, antigen-specific probes. The soluble TCR derivatives when appropriately labeled (or bound by a detectable ligand for that soluble TCR) can serve as a probe for specific peptide/MCHC complexes on cells, for example, derived surfaces of tumor cells or other neoplastic cells, or antigens diagnostic of virus-infected cells or other diseased cells. Other applications for high affinity TCR cell bound proteins or soluble derivatives include use in diagnosis or study of certain autoimmune diseases. Where a characteristic peptide/MHC or other marker surface antigen is known or can be identified, a high affinity, soluble TCR can be isolated for specific binding to that cell surface moiety and used in diagnosis or in therapy. The high affinity TCR proteins, desirably the soluble derivatives, can be used bound to cytotoxic agents as therapeutics in cancer treatment or other disorders where cells to be desirably destroyed have a characteristic and specific cell surface moiety which is recognized by a high affinity TCR (desirably a soluble TCR protein). Similarly, a soluble high affinity TCR as described herein can be coupled to an imaging agent and used to identify sites within the body where tumor cells reside where the TCR specifically binds a tumor cell marker with high affinity and specificity. A high affinity TCR bound to the surface of a cell or tissue which has been inappropriately targeted for autoimmune destruction can reduce autoimmune tissue destruction by cytotoxic lymphocytes by competing with those cytotoxic lymphocytes for binding to the cell surface of the targeted cells or tissue.

These results can also be considered in the context of an important, basic question in T cell responses. Are the low affinities previously observed for T cell receptors due to the absence of somatic mutations or due to in vivo selective pressures that act on the T cell? The high affinity receptors described in our study were derived by variation at the VJ junction, the same process that operates very effectively in T cells [Davis and Bjorkman (1988) supra]. The fact that we could readily isolate a diverse set of high affinity TCR in vitro indicates that there is no structural or genetic limitation to high affinity receptors. This supports the view that inherently low affinities of TCRs found in vivo are due to a lack of selection for higher affinity and perhaps a selection for lower affinity [Sykulev et al. (1995) *Proc. Natl. Acad. Sci. USA* 92:11990–11992; Rabinowitz et al. (1996) supra]. In this respect, the higher affinity TCRs now provide the reagents for directly testing hypotheses about the effects of affinity on T cell responses [Davis et al. (1998) supra; Sykulev et al. (1995) supra; Valitutti et al. (1995) supra; Rabinowitz et al. (1996) supra].

It will be appreciated by those of skill in the art that, due to the degeneracy of the genetic code, numerous functionally equivalent nucleotide sequences encode the same amino acid sequence.

Additionally, those of skill in the art, through standard mutagenesis techniques, in conjunction with the antigen-finding activity assays described herein, can obtain altered TCR sequences and test them for the expression of polypeptides having particular binding activity. Useful mutagenesis techniques known in the art include, without limitation, oligonucleotide-directed mutagenesis, region-specific mutagenesis, linker-scanning mutagenesis, and site-directed mutagenesis by PCR [see e.g. Sambrook et al. (1989) and Ausubel et al. (1999)].

In obtaining variant TCR coding sequences, those of ordinary skill in the art will recognize that TCR-derived proteins may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40–50° C., 6×SSC (sodium chloride/sodium citrate buffer) and 0.1% SDS (sodium dodecyl sulfate) indicate about 60–70% homology, hybridization and wash conditions of 50–65° C., 1×SSC and 0.1% SDS indicate about 82–97% homology, and hybridization and wash conditions of 52° C., 0.1×SSC and 0.1% SDS indicate about 99–100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the Internet at .ncbi.nlm.nih.gov and a version of ClustalW is available at 2.ebi.ac.uk.

Industrial strains of microorganisms (e.g., *Aspergillus niger, Aspergillus ficuum, Aspergillus awamori, Aspergillus oryzae, Trichoderma reesei, Mucor miehei, Kluyveromyces lactis, Pichia pastoris, Saccharomyces cerevisiae, Escherichia coli, Bacillus subtilis* or *Bacillus licheniformis*) or plant species (e.g., canola, soybean, corn, potato, barley, rye, wheat) may be used as host cells for the recombinant production of the TCR peptides. As the first step in the heterologous expression of a high affinity TCR protein or soluble protein, an expression construct is assembled to include the TCR or soluble TCR coding sequence and control sequences such as promoters, enhancers and terminators. Other sequences such as signal sequences and selectable markers may also be included. To achieve extracellular expression of the scTCR, the expression construct may include a secretory signal sequence. The signal sequence is not included on the expression construct if cytoplasmic expression is desired. The promoter and signal sequence are functional in the host cell and provide for expression and secretion of the TCR or soluble TCR protein. Transcriptional terminators are included to ensure efficient transcription. Ancillary sequences enhancing expression or protein purification may also be included in the expression construct.

Various promoters (transcriptional initiation regulatory region) may be used according to the invention. The selection of the appropriate promoter is dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in *E. coli*. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the invention. A signal sequence which is homologous to the TCR coding sequence may be used. Alternatively, a signal sequence which has been selected or designed for efficient secretion and processing in the expression host may also be used. For example, suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for *E. coli* host cells, nptII confers kanamycin resistance to a wide variety of prokaryotic and eukaryotic cells) or that permit the host to grow on minimal medium (e.g., HIS4 enables *P. pastoris* or His⁻ *S. cerevisiae* to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 $\mu$g of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli*. Numerous cloning vectors suitable for construction of the expression construct are known in the art ($\lambda$ZAP and pBLUESCRIPT SK-1, Stratagene, LaJolla, Calif., pET, Novagen Inc., Madison, Wis. —cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into *S. cerevisiae* cells by protoplast transformation or electroporation. Electroporation of *S. cerevisiae* is readily accomplished, and yields transformation efficiencies comparable to spheroplast transformation.

Monoclonal or polyclonal antibodies, preferably monoclonal, specifically reacting with a TCR protein at a site other than the ligand binding site may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1999) *Current Protocols in Molecular Biology*, John Wiley & Sons, Inc., New York.

High affinity TCR proteins in cell-bound or soluble form which are specific for a particular pMHC are useful, for example, as diagnostic probes for screening biological samples (such as cells, tissue samples, biopsy material, bodily fluids and the like) or for detecting the presence of the cognate pMHC in a test sample. Frequently, the high affinity TCR proteins are labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. Additionally the TCR protein can be coupled to a ligand for a second binding molecules: for example, the TCR protein can be biotinylated. Detection of the TCR bound to a target cell or molecule can then be effected by binding of a detectable streptavidin (a streptavidin to which a fluorescent, radioactive, chemiluminescent, or other detectable molecule is attached or to which an enzyme for which there is a chromophoric substrate available). U.S. patents describing the use of such labels and/or toxic compounds to be covalently bound to the scTCR protein include but are not limited to U.S. Pat. Nos. 3,817,837; 3,850,752; 3,927,193; 3,939,350; 3,996,345; 4,277,437; 4,275,149; 4,331,647; 4,348,376; 4,361,544; 4,468,457; 4,444,744; 4,640,561; 4,366,241; RE 35,500; 5,299,253; 5,101,827; 5,059,413. Labeled TCR proteins can be detected using a monitoring device or method appropriate to the label used. Fluorescence microscopy or fluorescence activated cell sorting can be used where the label is a fluorescent moiety, and where the label is a radionuclide, gamma counting, autoradiography or liquid scintillation counting, for example, can be used with the proviso that the method is appropriate to the sample being analyzed and the radionuclide used. In addition, there can be secondary detection molecules or particle employed where there is a detectable molecule or particle which recognized the portion of the TCR protein which is not part of the binding site for the cognate pMHC ligand or other ligand in the absence of a MHC component as noted herein. The art knows useful compounds for diagnostic imaging in situ; see, e.g., U.S. Pat. Nos. 5,101,827; 5,059,413. Radionuclides useful for therapy and/or imaging in vivo include $^{111}$Indium, $^{97}$Rubidium, $^{125}$Iodine, $^{131}$Iodine, $^{123}$Iodine, $^{67}$Gallium, $^{99}$Technetium. Toxins include diphtheria toxin, ricin and castor bean toxin, among others, with the proviso that once the TCR-toxin complex is bound to the cell, the toxic moiety is internalized so that it can exert its cytotoxic effect. Immunotoxin technology is well known to the art, and suitable toxic molecules include, without limitation, chemotherapeutic drugs such as vindesine, antifolates, e.g. methotrexate, cisplatin, mitomycin, anthrocyclines such as daunomycin, daunorubicin or adriamycin, and cytotoxic proteins such as ribosome inactivating proteins (e.g., diphtheria toxin, pokeweed antiviral protein, abrin, ricin, pseudomonas exotoxin A or their recombinant derivatives. See, generally, e.g., Olsnes and Pihl (1982) *Pharmac. Ther.* 25:355–381 and *Monoclonal Antibodies for Cancer Detection and Therapy*, Eds. Baldwin and Byers, pp. 159–179, Academic Press, 1985.

High affinity TCR proteins specific for a particular pMHC ligand are useful in diagnosing animals, including humans believed to be suffering from a disease associated with the particular pMHC. The sc TCR molecules of the present invention are useful for detecting essentially any antigen, including but not limited to, those associated with a neoplastic condition, an abnormal protein, or an infection or infestation with a bacterium, a fungus, a virus, a protozoan, a yeast, a nematode or other parasite. The high affinity sc TCR proteins can also be used in the diagnosis of certain genetic disorders in which there is an abnormal protein produced. Exemplary applications for these high affinity proteins is in the treatment of autoimmune diseases in which there is a known pMHC. Type I diabetes is relatively well characterized with respect to the autoantigens which attract immune destruction. Multiple sclerosis, celiac disease, inflammatory bowel disease, Crohn's disease and rheumatoid arthritis are additional candidate diseases for such application. High affinity TCR (soluble) proteins with binding specificity for the p/MHC complex on the surface of cells or tissues which are improperly targeted for autoimmune destruction can serve as antagonists of the autoimmune destruction by competing for binding to the target cells by cytotoxic lymphocytes. By contrast, high affinity TCR proteins, desirably soluble single chain TCR proteins, which specifically bind to an antigen or to a p/MHC on the surface of a cell for which destruction is beneficial, can be coupled to toxic compounds (e.g., toxins or radionuclides) so that binding to the target cell results in subsequent binding and destruction by cytotoxic lymphocytes. The cell targeted for destruction can be a neoplastic cell (such as a tumor cell), a cell infected with a virus, bacterium or protozoan or other disease-causing agent or parasite, or it can be a bacterium, yeast, fungus, protozoan or other undesirable cell. Such high affinity sc TCR proteins can be obtained by the methods described herein and subsequently used for screening for a particular ligand of interest.

The high affinity TCR compositions can be formulated by any of the means known in the art. They can be typically prepared as injectables, especially for intravenous, intraperitoneal or synovial administration (with the route determined by the particular disease) or as formulations for intranasal or oral administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes.

The active ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the high affinity TCR protein in injectable, aerosol or nasal formulations is usually in the range of 0.05 to 5 mg/ml. The selection of the particular effective dosages is known and performed without undue experimentation by one of ordinary skill in the art. Similar dosages can be administered to other mucosal surfaces.

In addition, if desired, vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween 80 emulsion. Such additional formulations and modes of administration as are known in the art may also be used.

The high affinity TCR proteins of the present invention and/or pMHC-binding fragments having primary structure similar (more than 90% identity) to the high affinity TCR proteins and which maintain the high affinity for the cognate ligand may be formulated into vaccines as neutral or salt forms. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylaminoethanol, histidine, and procaine.

High affinity TCR proteins for therapeutic use, e.g., those conjugated to cytotoxic compounds are administered in a manner compatible with the dosage formulation, and in such amount and manner as are prophylactically and/or therapeutically effective, according to what is known to the art. The quantity to be administered, which is generally in the range of about 100 to 20,000 $\mu$g of protein per dose, more generally in the range of about 1000 to 10,000 $\mu$g of protein per dose. Similar compositions can be administered in similar ways using labeled high affinity TCR proteins for use in imaging, for example, to detect tissue under autoimmune attack and containing the cognate pMHCs or to detect cancer cells bearing a cognate pMHC on their surfaces. Precise amounts of the active ingredient required to be administered may depend on the judgment of the physician or veterinarian and may be peculiar to each individual, but such a determination is within the skill of such a practitioner.

The vaccine or other immunogenic composition may be given in a single dose; two dose schedule, for example two to eight weeks apart; or a multiple dose schedule. A multiple dose schedule is one in which a primary course of vaccination may include 1 to 10 or more separate doses, followed by other doses administered at subsequent time intervals as required to maintain and/or reinforce the immune response, e.g., at 1 to 4 months for a second dose, and if needed, a subsequent dose(s) after several months. Humans (or other animals) immunized with the retrovirus-like particles of the present invention are protected from infection by the cognate retrovirus.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.)

(1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

All references cited in the present application are incorporated by reference herein to supplement the disclosure and experimental procedures provided in the present Specification to the extent that there is no inconsistency with the present disclosure.

The following examples are provided for illustrative purposes, and are not intended to limit the scope of the invention as claimed herein. Any variations in the exemplified articles and/or methods which occur to the skilled artisan are intended to fall within the scope of the present invention.

EXAMPLES

General methods for making high affinity TCRs are given in U.S. patent application Ser. No. 09/009,388, filed Jan. 20, 1998, and WO99/36569, filed Jan. 20, 1999, which are hereby incorporated by reference to the extent not inconsistent with the disclosure herewith.

Example 1

Library Construction

The 2C scTCR used as the scaffold for directed evolution (T7) contained six mutations ($\beta$G17E, $\beta$G42E $\beta$L81S, $\alpha$L43P, $\alpha$W82R, and $\alpha$I118N) that have been shown to increase the stability of the TCR but still allow pMHC binding [see, e.g., Shusta, E. V. et al. (1999) *J. Mol. Biol.* 292, 949–956].

Mutagenic PCR of the T7 scTCR V$\alpha$CDR3 was performed using an AGA2-specific upstream primer (GGCAGCCCCATAAACACACAGTAT (SEQ ID NO:3)) and a degenerate downstream primer CTTTTGT GCC GGATCCAAATGTCAG(SNN)$_5$GCTCACAGCACAGA AGTACACGGCCGAGTCGCTC (SEQ ID NO:4). Underlined bases indicate the positions of silent mutations introducing unique BamHI and EagI restriction sites. The purified PCR product was digested with NdeI and BamHI and ligated to NdeI-BamHI digested T7/pCT302 [Boder and Wittrup (1997) supra; Kieke et al. (1999) supra; Shusta et al. (1999) supra]. The ligation mixture was transformed into DH10B electro-competent *E. coli* (Gibco BRI, Gaithersburg, Md.), and transformants were pooled into 250 ml LB supplemented with ampicillin at 100 $\mu$g/ml and grown overnight at 37° C. Plasmid DNA was transformed into the yeast, (*Saccharomyces cerevisiae*) strain EBY100 by the method of Gietz and Schiestl [Geitz et al. (1995) *Yeast* 11:355–360].

Example 2

Cell Sorting

The yeast library [Shusta et al. (1999) *Curr. Opin. Biotechnol.* 10:117–122] was grown in SD-CAA (2% dextrose, 0.67% yeast nitrogen base, 1% casamino acids (Difco, Livonia, Mich.)) at 30° C. to an $OD_{600}$=4.0. To induce surface scTCR expression, yeast were pelleted by centrifugation, resuspended to an $OD_{600}$=1.0 in SG-CAA (2% galactose, 0.67% yeast nitrogen base, 1% casamino acids), and incubated at 20° C. for about 24 hr. In general, about $10^7$ cells/tube were incubated on ice for 1 hr with 50 $\mu$l of QL9/L$^d$/IgG dimers [Dal Porto et al. (1993) supra] diluted in phosphate buffered saline, pH 7.4 supplemented with 0.5 mg/ml BSA (PBS-BSA). After incubation, cells were washed and labeled for 30 min with FITC-conjugated goat anti-mouse IgG F(ab$^7$)$_2$ (Kirkegaard & Perry, Gaithersburg, Md.) in PBS-BSA. Yeast were then washed and resuspended in PBS-BSA immediately prior to sorting. Cells exhibiting the highest fluorescence were isolated by FACS sorting with a Coulter 753 bench. After isolation, sorted cells were expanded in SD-CAA and induced in SG-CAA for subsequent rounds of selection. A total of four sequential sorts were performed. The concentrations of QL9/L$^d$/IgG dimers used for staining were 50 $\mu$g/ml for sorts 1–3 and 0.5 $\mu$g/ml for the final sort. The percentages of total cells isolated from each sort were 5.55, 2.68, 2.56, and 0.58%, respectively. Aliquots of sorts 3 and 4 were plated on SD-CAA to isolate individual clones which were analyzed by flow cytometry using a Coulter Epics XL instrument.

Example 3

Soluble scTCR Production

The T7 and qL2 open reading frames were excised from pCT302 NheI-XhoI and ligated into NheI-XhoI digested pRSGALT, a yeast expression plasmid [Shusta et al. (1999) supra]. Ligated plasmids were transformed into DH10B electro-competent *E. coli* (Gibco BRL). Plasmid DNA was isolated from bacterial cultures and transformed into *Saccharomyces cerevisiae* BJ5464 ($\alpha$ ura3–52 trp1 leu2 1 his3 200pep4::HIS3 prb1 1.6R can1 GAL) [Shusta et al. (1999) supra]. Yeast clones were grown in one liter SD-CAA/Trp (20 mg/L tryptophan) for 48 hr at 30° C. To induce scTCR secretion, cells were pelleted by centrifugation at 4000×g, resuspended in one liter SG-CAA/Trp supplemented with 1 mg/ml BSA, and incubated for 72 hr at 20° C. Culture supernatants were harvested by centrifugation at 4000×g, concentrated to about 50 ml, and dialyzed against PBS, pH 8.0. The 6His-tagged scTCRs were purified by native nickel affinity chromatography (Ni-NTA Superflow, Qiagen, Valencia, Calif.; 5 mM and 20 mM imidazole, pH 8.0 wash; 250 mM imidazole elution) [Shusta et al. (1999) supra].

Example 4

Cell-Binding Assays

The binding of soluble scTCRs to QL9/L$^d$ was monitored in a competition format as described previously [Manning et al. (1998) supra; Sykulev et al. (1994) supra]. Peptide-upregulated T2-L$^d$ cells (3×10$^5$/well) were incubated for one hour on ice in the presence of $^{125}$I-labeled anti-L$^d$ Fabs (30-5-7) and various concentrations of scTCRs. Bound and unbound $^{125}$I 30-5-7 Fabs were separated by centrifugation through olive oil/dibutyl phthalate. Inhibition curves were constructed to determine inhibitor concentrations yielding 50% of maximal inhibition. Dissociation constants were calculated using the formula of Cheng and Pursoff [Cheng (1973) *Biochem. Pharm.* 22:3099–3108]. To monitor direct binding of scTCRs to cell-bound pMHC, peptide-upregulated T2-L$^d$ cells (5×10$^5$/tube) were incubated for 40 min on ice with biotinylated soluble scTCRs followed by staining for 30 min with streptavidin-phycoerythrin (PharMingen, San Diego, Calif.). Cellular fluorescence was detected by flow cytometry.

Example 5

Identification of High Affinity TCRs that are Specific for a Different Peptide and a Different MHC Molecule (K$^b$)

Using the same library of yeast-displayed mutants of the CDR3$\alpha$ region of the TCR, it was possible to select for higher affinity TCRs that are specific for yet a different peptide bound to a different MHC molecule. In this case the peptide called SIYR (SIYRYYGL (SEQ ID NO:5)) was bound to the MHC molecule called $K^b$, and this ligand complex was used in fluorescent form to select by flow cytometry. Sixteen clones expressing high affinity TCR were sequenced, each showing a different sequence in the CDR3α region FIG. 11.

Figure 5:
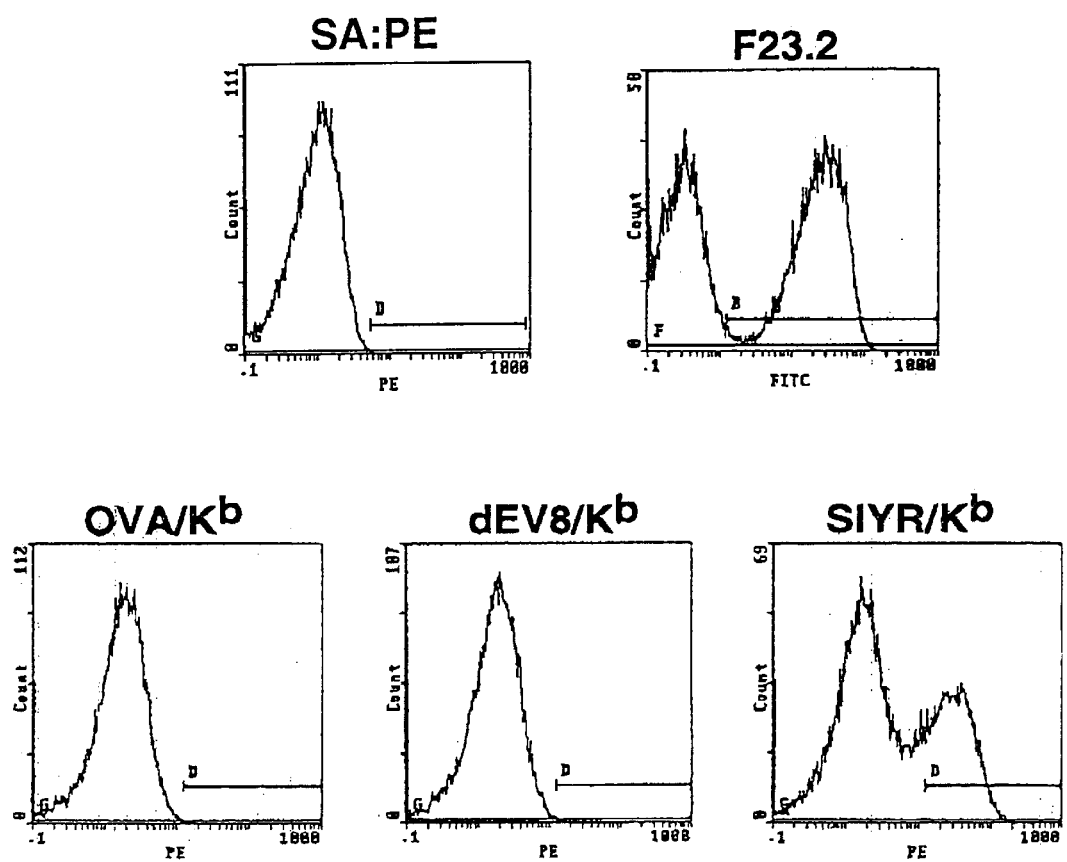
FIG. 5: Flow cytometry histograms of yeast displaying a mutant scTCR (called 3SQ2) stained with biotinylated peptide/MHC complexes, OVA/$K^b$, dEV8/$K^b$ or SIYR (SEQ ID NO:2)/$K^b$, followed by streptavidin-PE. As a positive control for the presence of scTCR, yeast were stained with the Vβ-specific Ig, F23.2 followed by FITC goat-anti-mouse F(ab')$_2$.

As an example of the specificity of these TCRs, the mutant 3SQ2 was stained with various agents, including the secondary reagent alone (SA:PE), the anti-Vβ antibody F23.2, and three peptide/$K^b$ complexes (OVA/$K^b$, dEV8/$K^b$, and SIYR/$K^b$). As shown in FIG. 5, only the pMHC (SIYR/$K^b$) used in the original selection had sufficient affinity to bind to the mutant TCR. Wild-type TCR did not bind the SIYR/$K^b$ ligand at any concentration tested (data not shown).

The mutant TCR 3SQ2 was also expressed as a soluble protein in the yeast secretion system and tested after biotinylation for its ability to bind directly to pMHC on the surface of tumor cells. As shown in FIG. 6, the labeled 3SQ2 bound very well to tumor cells that expressed only the appropriate peptide SIYR. The staining was nearly as strong as the high affinity anti-$K^b$ monoclonal antibody B8.24.3, that binds to any $K^b$ molecule (FIG. 6), regardless of the peptide present.

Example 6

Identification of High Affinity TCRs that are Specific for a Different Peptide Bound to the Same MHC Molecule ($K^b$)

Figure 7:
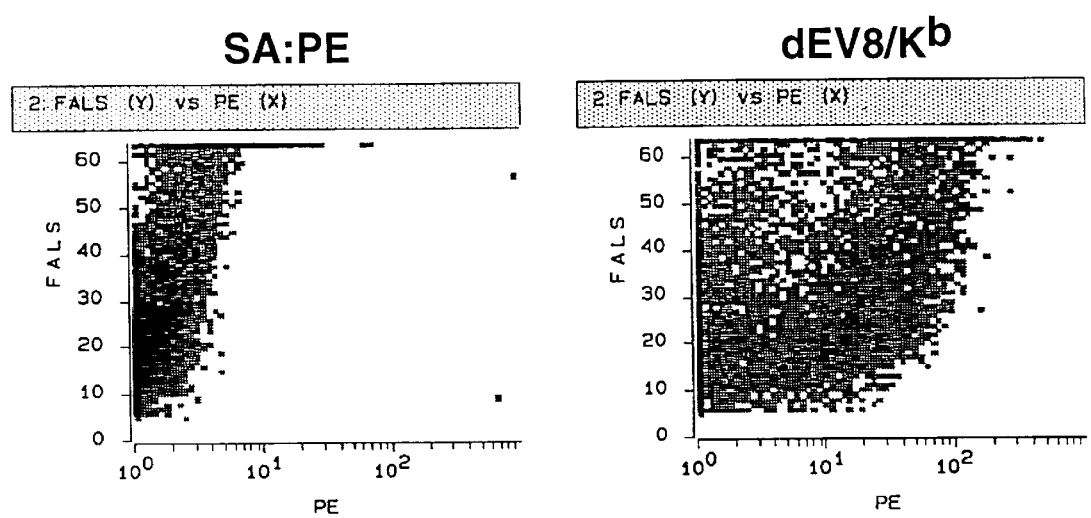
FIG. 7: After multiple rounds of sorting with dEV8/$K^b$, the yeast VαCDR3 library was stained with biotinylated dEV8/$K^b$ followed by streptavidin-PE and analyzed by flow cytometry.

To determine if the same TCR scaffold could be used to isolate higher affinity forms against yet a different peptide bound to the same MHC, we screened the TCR CDR3α library with the peptide called dEV8 (EQYKFYSV (SEQ ID NO:6)), bound to $K^b$. After several sorts by flow cytometry with the biotinylated dEV$_8$/$K^b$ ligand (followed by phycoerythrin-streptavidin, PE-SA), there was a significant enrichment of yeast cells that bound to the dEV8/$K^b$ (as indicated by PE levels in FIG. 7).

Six of the clones that were isolated by selection with dEV8/$K^b$ were sequenced and the CDR3 sequences all differed FIG. 12. These sequences were similar in sequence, but different from, those isolated by selection with SIYR/$K^b$ (two examples, 3SQ2 and 3SQ5, are also shown in FIG. 12. It can be concluded that it is possible to isolate higher affinity TCRs against different antigens, even using the same TCR library of mutants.

To prove the antigen specificity of the isolated clones, one of the dEV$_8$/$K^b$ selected clones (4d1) was examined with a panel of different antibodies and ligands (FIG. 6). As expected, this TCR reacted with the three appropriate antibodies (anti-Vβ8 antibody F23.2, anti-HA tag antibody, and anti-His tag antibody) and the dEV8/$K^b$ antigen, but not with another antigen, OVA/$K^b$. Wild type TCR did not bind to either peptide/$K^b$ complex (data not shown). Thus, the high affinity TCR was specific for the selected antigen.

Example 7

Identification of High Affinity TCRs by Creating a Random TCR Library in a Different Region of the TCR (Complementarity-Determining Region 3 of the β Chain)

Figure 8:
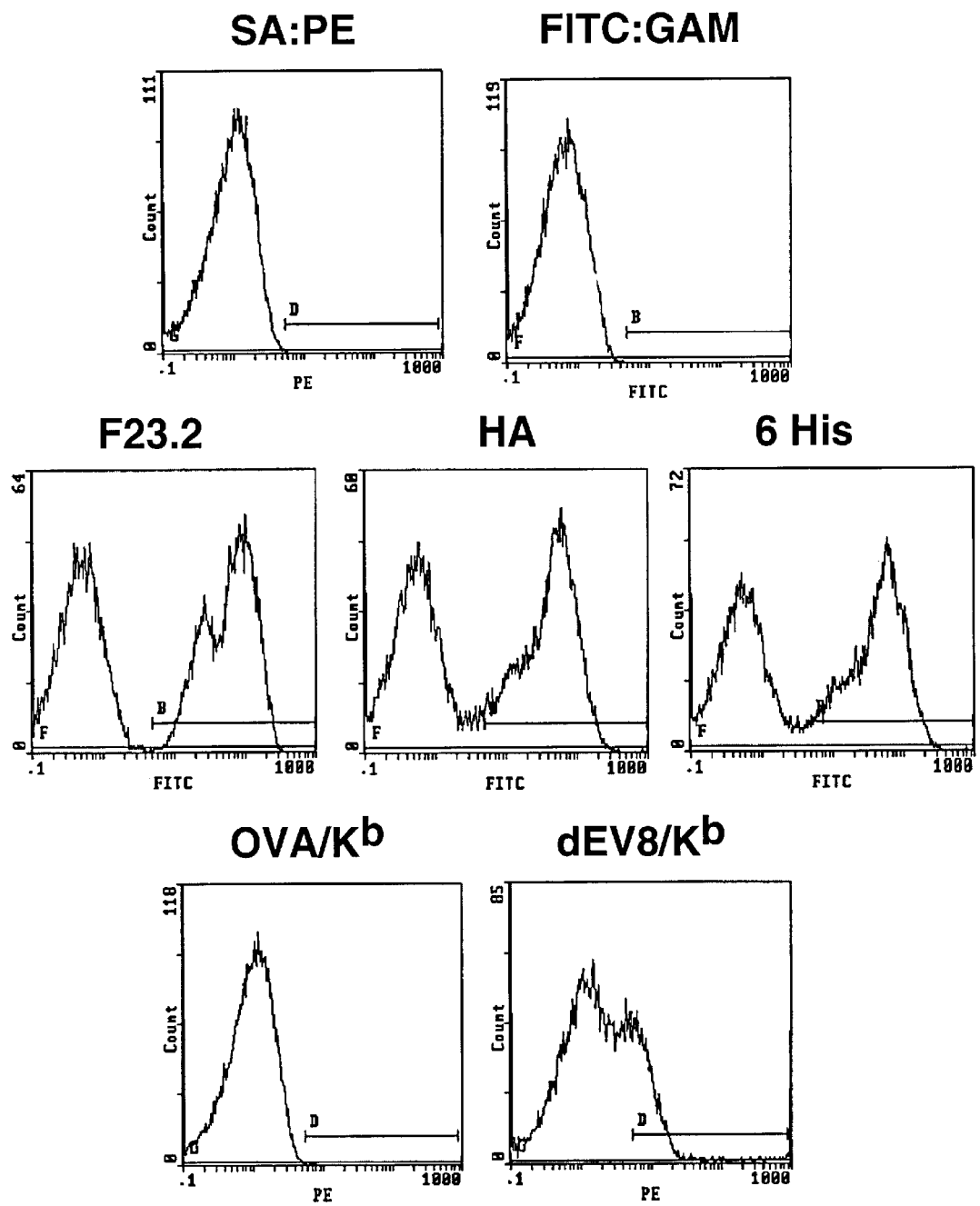
FIG. 8: Flow cytometry histograms of yeast displaying a mutant scTCR (called 4d1) stained with biotinylated peptide/MHC complexes, OVA/$K^b$ or dEV8/$K^b$ followed by staining with biotinylated streptavidin-PE. As positive controls the yeast were analyzed for the presence of scTCR Vβ with F23.2 Ig and for epitope tags with an anti-6His antibody or the anti-HA Ig, 12CA5.
Figure 9:
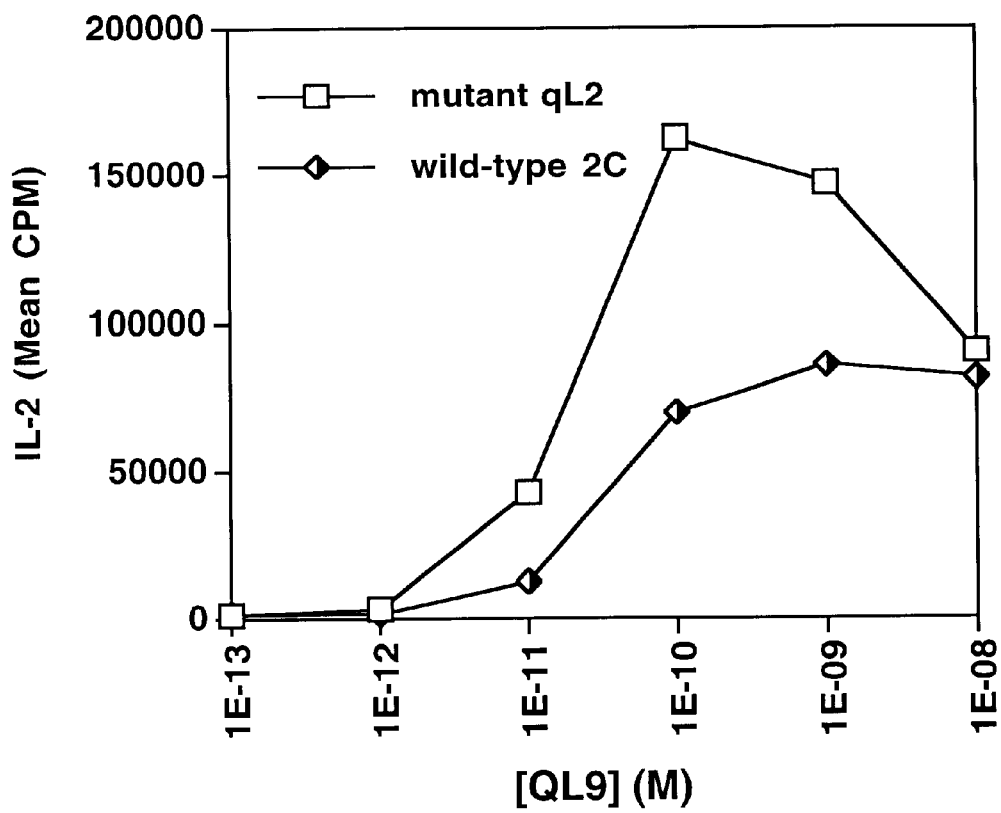
FIG. 9: T cells transfected with the mutant T cell receptor qL2 can recognize and be stimulated by target cells that express the peptide-MHC at low concentrations. T-cell hybridoma cell line 58−/− (Letourneur, F., and B. Malissen. (1989) *Eur J Immunol* 19(12), 2269–74) was transfected with the wild-type (2C) or mutant (qL2) TCRs and 7.5×10$^4$ transfected cells/well were incubated at 37° C. with T2-Ld cells (7.5×10$^4$/well) in the presence of QL9 peptide. After ~30 hrs, supernatants were collected and assayed for IL-2 released by the T cells: Supernatants were incubated with the IL-2 dependent cell line, HT2 (5×10$^3$/well) for 18 hrs at 37° C. Proliferation of HT2 cells was measured by the incorporation of 3 [H] thymidine. Mean CPM represents the average of triplicate wells. No IL-2 was released in the absence of the QL9 peptide (data not shown).

The examples described above used a library of TCR that were mutated within a region of the α chain called CDR3. In order to show that other regions of the TCR could also be mutated to yield higher affinity TCR, a library of random mutants within five contiguous amino acid residues of the CDR3 region of the β chain was produced, using the qL2 TCR mutant as the starting material. This library was then selected with the QL9/$L^d$ ligand at concentrations below that detected with the qL2 mutant. Five yeast clones, selected by flow cytometry, were sequenced and each showed a different nucleotide and amino acid sequence (FIG. 8). There was remarkable conservation of sequence within the five amino acid region that was mutated, suggesting that this sequence motif has been optimized for high affinity. We conclude that it is possible to mutate different regions of the TCR to yield derivatives having higher affinity for a particular pMHC.

Although the description above contains many specificities, these should not be construed to limit the scope of the invention but as merely providing illustrations of some of the presently-preferred embodiments of this invention. For example, ligands other than those specifically illustrated may be used. Thus the scope of the invention should be determined by the appended claims and their legal equivalents, rather than by the examples given. All references cited herein are incorporated to the extent not inconsistent with the disclosure herewith.

We claim:

1. A soluble T cell receptor (TCR) having high affinity for a ligand exhibiting a dissociation constant for that ligand greater than about $10^7 M^{-1}$, wherein said TCR is a mutant TCR carrying one or more mutations in a CDR.

2. The soluble T cell receptor of claim 1 wherein the TCR exhibits a dissociation constant for the ligand between about $10^7$ to $10^{10} M^{-1}$.

3. The soluble TCR of claim 1 wherein the ligand is a peptide/MHC ligand.

4. The soluble TCR of claim 1 wherein the ligand is a superantigen.

5. The soluble TCR of claim 1 which is a mutant TCR carrying one or more mutations in a CDR.

6. The soluble TCR of claim 5 wherein the one or more mutations are in CDR3α or CDR3β.

7. A soluble mutant T cell receptor (TCR) having high affinity for a ligand and having one or more mutations in a CDR.

8. The soluble TCR of claim 7 wherein the one or more mutations are in CDR3α or CDR3β.

9. The soluble TCR of claim 7 wherein the ligand is a peptide/MHC ligand.

10. The soluble TCR of claim 7 wherein the ligand is a superantigen.

11. An isolated T cell expressing on its surface high affinity TCR's exhibiting a dissociation constant greater than $10^7 M^{-1}$ for a selected ligand, wherein said TCR is a mutant TCR carrying one or more mutations in a CDR.

12. The T cell of claim 11 wherein the TCR exhibits a dissociation constant between about $10^7$ to $10^{10} M^{-1}$ for said ligand.

13. The T cell of claim 11 wherein the ligand is a peptide/MHC ligand.

14. The T cell of claim 11 wherein the ligand is a superantigen.

15. The T cell of claim 11 wherein the high affinity TCR is a mutant carrying one or more mutations in a CDR.

16. The T cell of claim 11 wherein the high affinity TCR is a mutant carrying one or more mutations in CDR3α or CDR3β.

17. An isolated T cell expressing on its surface a high affinity TCR carrying one or more mutations in a CDR.

18. The T cell of claim 17 wherein the high affinity TCR is a mutant carrying one or more mutations in a CDR3α or CDR3β.

19. The T cell of claim 17 wherein the ligand is a peptide/MHC ligand.

20. The T cell of claim 17 wherein the ligand is a superantigen.

21. A soluble mutant T cell receptor (TCR) having an high affinity for a ligand and having one or more mutations in a CDR where the TCR exhibits a dissociation constant for the ligand from about $10^{10} M^{-1}$.

22. The soluble TCR of claim 21 wherein the one or ore mutations are in CDR3α or CDR3β.

23. The soluble TCR of claim 21 wherein the ligand is a peptide/HMC ligand.

* * * * *

UNITED STATES PATENT AND TRADEMARK OFFICE
CERTIFICATE OF CORRECTION

PATENT NO. : 6,759,243 B2
APPLICATION NO. : 09/731242
DATED : July 6, 2004
INVENTOR(S) : Kranz et al.

It is certified that error appears in the above-identified patent and that said Letters Patent is hereby corrected as shown below:

On the title page item (56), add --6,300,065 B1 10/2001 Kieke et al.-- to the list of U.S. Patent Documents, left column on page 2, line 27, On the title page item (56), add --WO 93/JP408 1993-- to the list of Foreign Patent Documents, left column on page 2, line 51, In column 2, line 25, please replace "$V_\alpha C_\alpha V_{\beta C\beta}$" with --$V_\alpha C_\alpha V_\beta C_\beta$--.

In column 4, line 35, replace "cytoxic" with --cytotoxic--.

In column 44, line 32, 4th line in claim 21, replace "ligand from about $10^{10} M^{-1}$" with --ligand from about $10^7$ to about $10^{10} M^{-1}$--.

In column 44, line 36, second line in claim 23, replace "HMC ligand" with --MHC ligand--.

Signed and Sealed this

Seventeenth Day of April, 2007

JON W. DUDAS
*Director of the United States Patent and Trademark Office*

(12) EX PARTE REEXAMINATION CERTIFICATE (10164th)
United States Patent
Kranz et al.

(10) Number: US 6,759,243 C1
(45) Certificate Issued: May 15, 2014

(54) HIGH AFFINITY TCR PROTEINS AND METHODS

(75) Inventors: David M. Kranz, Champaign, IL (US); K. Dane Wittrup, Chestnut Hill, MA (US); Phillip D. Holler, Champaign, IL (US)

(73) Assignees: The United States of America as represented by the National Institutes of Health (NIH), Washington, DC (US); The United States of America as represented by the Dept. of Health and Human Services (DHHS), Washington, DC (US)

Reexamination Request:
No. 90/012,803, Mar. 8, 2013

Reexamination Certificate for:
Patent No.: 6,759,243
Issued: Jul. 6, 2004
Appl. No.: 09/731,242
Filed: Dec. 6, 2000

Certificate of Correction issued Apr. 17, 2007

Related U.S. Application Data

(63) Continuation-in-part of application No. 09/009,388, filed on Jan. 20, 1998, now Pat. No. 6,699,658.

(60) Provisional application No. 60/169,179, filed on Dec. 6, 1999.

(51) Int. Cl.
*C07K 14/725* (2006.01)
*C12N 5/00* (2006.01)
*C12N 15/10* (2006.01)
*C40B 40/02* (2006.01)
*G01N 33/68* (2006.01)

(52) U.S. Cl.
USPC .................... 435/372.3; 435/320.1; 435/325; 435/366; 435/372; 530/350

(58) Field of Classification Search
None
See application file for complete search history.

(56) References Cited

To view the complete listing of prior art documents cited during the proceeding for Reexamination Control Number 90/012,803, please refer to the USPTO's public Patent Application Information Retrieval (PAIR) system under the Display References tab.

*Primary Examiner* — Bruce Campell

(57) ABSTRACT

T cell receptors (TCRs) that have higher affinity for a ligand than wild type TCRs are provided. These high affinity TCRs are formed by mutagenizing a T cell receptor protein coding sequence to generate a variegated population of mutants of the T cell receptor protein coding sequence; transforming the T cell receptor mutant coding sequence into yeast cells; inducing expression of the T cell receptor mutant coding sequence on the surface of yeast cells; and selecting those cells expressing T cell receptor mutants that have higher affinity for the peptide/MHC ligand than the wild type T cell receptor protein. The high affinity TCRs can be used in place of an antibody or single chain antibody.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 7-10 and 17-20 is confirmed.

Claims 5 and 15 are cancelled.

Claims 1, 11 and 21 are determined to be patentable as amended.

Claims 2-4, 6, 12-14, 16, 22 and 23, dependent on an amended claim, are determined to be patentable.

1. A soluble T cell receptor (TCR) having high affinity for a ligand exhibiting [a dissociation constant] *an affinity* for that ligand greater than about $10^7$ $M^{-1}$, wherein said TCR is a mutant TCR carrying one or more mutations in a CDR.

11. An isolated T cell expressing on its surface high affinity TCR's exhibiting [a dissociation constant] *an affinity* greater than $10^7$ $M^{-1}$ for a selected ligand, wherein said TCR is a mutant TCR carrying one or more mutations in a CDR.

21. A soluble mutant T cell receptor (TCR) having [an] high affinity for a ligand and having one or more mutations in a CDR where the TCR exhibits [a dissociation constant] *an affinity* for the ligand from about $10^7$ to about $10^{10}$ $M^{-1}$.

* * * * *

(12) EX PARTE REEXAMINATION CERTIFICATE (10723rd)
United States Patent
Kranz et al.

(10) Number: US 6,759,243 C2
(45) Certificate Issued: Sep. 29, 2015

(54) HIGH AFFINITY TCR PROTEINS AND METHODS

(75) Inventors: David M. Kranz, Champaign, IL (US); K. Dane Wittrup, Chestnut Hill, MA (US); Phillip D. Holler, Champaign, IL (US)

(73) Assignee: NATIONAL INSTITUTES OF HEALTH (NIH), U.S. DEPT. OF HEALTH AND HUMAN SERVICES (DHHS), THE UNITED STATES OF AMERICA, Washington, DC (US)

Reexamination Request:
No. 90/013,274, Jun. 18, 2014

Reexamination Certificate for:
Patent No.: 6,759,243
Issued: Jul. 6, 2004
Appl. No.: 09/731,242
Filed: Dec. 6, 2000

Reexamination Certificate C1 6,759,243 issued May 15, 2014

Certificate of Correction issued Apr. 17, 2007

Related U.S. Application Data

(63) Continuation-in-part of application No. 09/009,388, filed on Jan. 20, 1998, now Pat. No. 6,699,658.

(60) Provisional application No. 60/169,179, filed on Dec. 6, 1999.

(51) Int. Cl.
*C12N 15/10* (2006.01)
*C12N 5/00* (2006.01)
*C07K 14/725* (2006.01)
*C40B 40/02* (2006.01)
*G01N 33/68* (2006.01)

(52) U.S. Cl.
CPC ........ *C07K 14/7051* (2013.01); *C12N 15/1037* (2013.01); *C12N 15/10* (2013.01); *G01N 33/68* (2013.01); *G01N 2333/39* (2013.01)

(58) Field of Classification Search
None
See application file for complete search history.

(56) References Cited

To view the complete listing of prior art documents cited during the proceeding for Reexamination Control Number 90/013,274, please refer to the USPTO's public Patent Application Information Retrieval (PAIR) system under the Display References tab.

*Primary Examiner* — Jerry D Johnson

(57) ABSTRACT

T cell receptors (TCRs) that have higher affinity for a ligand than wild type TCRs are provided. These high affinity TCRs are formed by mutagenizing a T cell receptor protein coding sequence to generate a variegated population of mutants of the T cell receptor protein coding sequence; transforming the T cell receptor mutant coding sequence into yeast cells; inducing expression of the T cell receptor mutant coding sequence on the surface of yeast cells; and selecting those cells expressing T cell receptor mutants that have higher affinity for the peptide/MHC ligand than the wild type T cell receptor protein. The high affinity TCRs can be used in place of an antibody or single chain antibody.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5 and 15 were previously cancelled.

Claims 1-4, 6, 9, 11-14, 16, 19 and 21-23 are cancelled.

Claims 7 and 17 are determined to be patentable as amended.

Claims 8, 10, 18 and 20, dependent on an amended claim, are determined to be patentable.

7. A soluble mutant T cell receptor (TCR) having high affinity for a ligand and having one or more mutations in a CDR, *wherein the ligand is a peptide/MHC ligand and wherein the soluble mutant TCR has at least about 100-fold higher affinity for the ligand than the wild type TCR.*

17. An isolated T cell expressing on its surface a high affinity TCR carrying one or more mutations in a CDR, *wherein the high affinity TCR has at least about 100-fold higher affinity for a peptide/MHC ligand than the wild type TCR.*

\* \* \* \* \*

SEQUENCE LISTING

```
<160> NUMBER OF SEQ ID NOS: 53

<210> SEQ ID NO 1
<211> LENGTH: 4
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: null peptide

<400> SEQUENCE: 1

Met Cys Met Val
1
```

```
<210> SEQ ID NO 2
<211> LENGTH: 4
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: incubation peptide

<400> SEQUENCE: 2

Ser Ile Tyr Arg
1

<210> SEQ ID NO 3
<211> LENGTH: 24
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: upstream primer

<400> SEQUENCE: 3

Gly Gly Cys Ala Gly Cys Cys Cys Ala Thr Ala Ala Ala Cys Ala
1               5                  10                  15

Cys Ala Cys Ala Gly Thr Ala Thr
            20

<210> SEQ ID NO 4
<211> LENGTH: 74
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: downstream primer

<400> SEQUENCE: 4

Cys Thr Thr Thr Thr Gly Thr Gly Cys Cys Gly Gly Ala Thr Cys Cys
1               5                  10                  15

Ala Ala Ala Thr Gly Thr Cys Ala Gly Ser Asn Asn Ser Asn Asn Ser
            20                  25                  30

Asn Asn Ser Asn Asn Ser Asn Asn Gly Cys Thr Cys Ala Cys Ala Gly
        35                  40                  45

Cys Ala Cys Ala Gly Ala Ala Gly Thr Ala Cys Ala Cys Gly Gly Cys
    50                  55                  60

Cys Gly Ala Gly Thr Cys Gly Cys Thr Cys
65                  70

<210> SEQ ID NO 5
<211> LENGTH: 8
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: binding peptide

<400> SEQUENCE: 5

Ser Ile Tyr Arg Tyr Tyr Gly Leu
1               5

<210> SEQ ID NO 6
<211> LENGTH: 8
<212> TYPE: PRT
<213> ORGANISM: ARTIFICIAL SEQUENCE
```

```
<220> FEATURE:
<221> NAME/KEY: misc_feature
<222> LOCATION: ()..()
<223> OTHER INFORMATION: screening peptide

<400> SEQUENCE: 6

Glu Gln Tyr Lys Phe Tyr Ser Val
1               5

<210> SEQ ID NO 7
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 7

Ser Gly Phe Ala Ser Ala Leu
1               5

<210> SEQ ID NO 8
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 8

Ser Ser Tyr Gly Asn Tyr Leu
1               5

<210> SEQ ID NO 9
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 9

Ser Arg Arg Gly His Ala Leu
1               5

<210> SEQ ID NO 10
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 10

Ser Ser Arg Gly Thr Ala Leu
1               5

<210> SEQ ID NO 11
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence
```

```
<400> SEQUENCE: 11

Ser His Phe Gly Thr Arg Leu
1               5

<210> SEQ ID NO 12
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 12

Ser Met Phe Gly Thr Arg Leu
1               5

<210> SEQ ID NO 13
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 13

Ser His Gln Gly Arg Tyr Leu
1               5

<210> SEQ ID NO 14
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 14

Ser Tyr Leu Gly Leu Arg Leu
1               5

<210> SEQ ID NO 15
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 15

Ser Lys His Gly Ile His Leu
1               5

<210> SEQ ID NO 16
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 16

Ser Leu Thr Gly Arg Tyr Leu
```

```
<210> SEQ ID NO 17
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 17

Ser Leu Pro Pro Pro Leu Leu
1               5

<210> SEQ ID NO 18
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 18

Ser Ile Pro Thr Pro Ser Leu
1               5

<210> SEQ ID NO 19
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 19

Ser Asn Pro Pro Pro Leu Leu
1               5

<210> SEQ ID NO 20
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 20

Ser Asp Pro Pro Pro Leu Leu
1               5

<210> SEQ ID NO 21
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 21

Ser Ser Pro Pro Pro Arg Leu
1               5

<210> SEQ ID NO 22
```

```
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 22

Ser Ala Pro Pro Ile Leu
1               5

<210> SEQ ID NO 23
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 23

Ser Gly Thr His Pro Phe Leu
1               5

<210> SEQ ID NO 24
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 24

Ser Gly His Leu Pro Phe Leu
1               5

<210> SEQ ID NO 25
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 25

Ser Asp Ser Lys Pro Phe Leu
1               5

<210> SEQ ID NO 26
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 26

Ser Ser Asp Arg Pro Tyr Leu
1               5

<210> SEQ ID NO 27
<211> LENGTH: 7
<212> TYPE: PRT
<213> ORGANISM: ARTIFICIAL SEQUENCE
<220> FEATURE:
```

-continued

<221> NAME/KEY: misc_feature
<222> LOCATION: ()..()
<223> OTHER INFORMATION: CDR3alpha sequence

<400> SEQUENCE: 27

Ser Leu Glu Arg Pro Tyr Leu
1               5

<210> SEQ ID NO 28
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 28

Ser Arg Glu Ala Pro Tyr Leu
1               5

<210> SEQ ID NO 29
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 29

Ser Leu His Arg Pro Ala Leu
1               5

<210> SEQ ID NO 30
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 30

Ser Leu His Arg Pro Ala Leu
1               5

<210> SEQ ID NO 31
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 31

Ser Ser Asn Arg Pro Ala Leu
1               5

<210> SEQ ID NO 32
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence -continued

```
<400> SEQUENCE: 32

Ser Thr Asp Arg Pro Ser Leu
1               5

<210> SEQ ID NO 33
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 33

Ser Gly Ser Arg Pro Thr Leu
1               5

<210> SEQ ID NO 34
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 34

Ser Leu Val Thr Pro Ala Leu
1               5

<210> SEQ ID NO 35
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 35

Ser Ala Thr Ser Pro Ala Leu
1               5

<210> SEQ ID NO 36
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 36

Ser Ser Ile Asn Pro Ala Leu
1               5

<210> SEQ ID NO 37
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 37

Ser Ala Ser Tyr Pro Ser Leu
1               5
```

```
<210> SEQ ID NO 38
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 38

Ser Arg Trp Thr Ser Gly Leu
1               5

<210> SEQ ID NO 39
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 39

Ser Gly Ser Arg Pro Ala Leu
1               5

<210> SEQ ID NO 40
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 40

Ser Leu Thr His His Phe Leu
1               5

<210> SEQ ID NO 41
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 41

Ser Met Thr His His Phe Leu
1               5

<210> SEQ ID NO 42
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 42

Ser Leu Ser Arg Pro Tyr Leu
1               5

<210> SEQ ID NO 43
<211> LENGTH: 7
```

```
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 43

Ser Leu Thr Arg Pro Tyr Leu
1               5

<210> SEQ ID NO 44
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 44

Ser Thr Tyr Arg His Tyr Leu
1               5

<210> SEQ ID NO 45
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 45

Ser Gly Leu Ala Arg Pro Leu
1               5

<210> SEQ ID NO 46
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 46

Ser Leu His Arg Pro Ala Leu
1               5

<210> SEQ ID NO 47
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3alpha sequence

<400> SEQUENCE: 47

Ser Gly Thr His Pro Phe Leu
1               5

<210> SEQ ID NO 48
<211> LENGTH: 7
<212> TYPE: PRT
<213> ORGANISM: ARTIFICIAL SEQUENCE
<220> FEATURE:
<221> NAME/KEY: misc_feature
```

```
<222> LOCATION: ()..()
<223> OTHER INFORMATION: CDR3beta sequence

<400> SEQUENCE: 48

Gly Gly Gly Gly Thr Leu Tyr
1               5

<210> SEQ ID NO 49
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3beta sequence

<400> SEQUENCE: 49

Gly Gly Gly Gly Val Leu Tyr
1               5

<210> SEQ ID NO 50
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3beta sequence

<400> SEQUENCE: 50

Gly Leu Gly Gly Ile Leu Tyr
1               5

<210> SEQ ID NO 51
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3beta sequence

<400> SEQUENCE: 51

Gly Gln Gly Gly Val Leu Tyr
1               5

<210> SEQ ID NO 52
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3beta sequence

<400> SEQUENCE: 52

Gly Ser Gly Gly Ile Ile Tyr
1               5

<210> SEQ ID NO 53
<211> LENGTH: 7
<212> TYPE: PRT
<213> ORGANISM: ARTIFICIAL SEQUENCE
<220> FEATURE:
<221> NAME/KEY: misc_feature
<222> LOCATION: ()..()
<223> OTHER INFORMATION: CDR3beta sequence
```

```
-continued

<400> SEQUENCE: 53

Gly Gly Gly Gly Ile Leu Tyr
1               5
```